US012784194B2

(12) United States Patent
Saqi et al.

(10) Patent No.: US 12,784,194 B2
(45) Date of Patent: Nov. 3, 2026

(54) PATHOLOGICAL RESPONSE CALCULATION AND ASSESSMENT TOOL

(71) Applicant: Genentech, Inc., South San Francisco, CA (US)

(72) Inventors: Anjali Saqi, New York, NY (US); Shawn Wen Sun, El Cerrito, CA (US); Kosei Tajima, Saitama (JP); Barbara Jennifer Gitlitz, Los Angeles, CA (US)

(73) Assignee: GENENTECH, INC., South San Francisco, CA (US)

( * ) Notice: Subject to any disclaimer, the term of this patent is extended or adjusted under 35 U.S.C. 154(b) by 619 days.

(21) Appl. No.: 18/357,772

(22) Filed: Jul. 24, 2023

(65) Prior Publication Data

US 2024/0062368 A1 Feb. 22, 2024

Related U.S. Application Data

(63) Continuation of application No. PCT/US2022/013567, filed on Jan. 24, 2022.

(60) Provisional application No. 63/141,377, filed on Jan. 25, 2021.

(51) Int. Cl.
*G06T 7/00* (2017.01)
*G16B 15/00* (2019.01)

(52) U.S. Cl.
CPC ............ *G06T 7/0012* (2013.01); *G16B 15/00* (2019.02); *G06T 2200/24* (2013.01); *G06T 2207/30024* (2013.01)

(58) Field of Classification Search
CPC ............... G06T 7/0012; G06T 2200/24; G06T 2207/30024; G16B 15/00; G16H 10/20
See application file for complete search history.

(56) References Cited

U.S. PATENT DOCUMENTS 12,141,968 B2 11/2024 Saqi et al.
2021/0216822 A1 * 7/2021 Paik ........................ G10L 15/22
2022/0237778 A1 7/2022 Saqi et al.

OTHER PUBLICATIONS

"SPSS Base 15.0 User's Guide". SPSS Inc. 2006 (Year: 2006).*
(Continued)

*Primary Examiner* — John R Wallace
(74) *Attorney, Agent, or Firm* — MORRISON & FOERSTER LLP

(57) ABSTRACT

In one embodiment, a method includes, for each of a set of samples, receiving data input that includes dimensions of a sample area, a percentage of the sample area being viable cells, and a percentage of the sample area exhibiting necrosis. The method includes, for each of the set of samples, computing a percentage of the sample area being stroma. The method includes, for each of the set of samples, computing weighting factors. The method includes computing a weighted percentage of the set of samples being viable cells based on the computed weighting factor and percentage of the sample area being viable cells for each of the set of samples. The method includes determining that a specified condition is detected in the set of samples based on the computed weighted percentage of the set of samples being viable cells satisfying a threshold correlating with an indication of the specified condition.

20 Claims, 12 Drawing Sheets

100 Mean % Viable Cells Calculation

| | 110 | Sample Dimensions | | | Area | | |
|---|---|---|---|---|---|---|---|
| Slide | Slide # (e.g. A1, A2, etc) | 115 Width [cm] | 120 Length [cm] | 125 % Viable cells / sample bed | 130 Width x Length | 135 Weighted | 140 Mean % Viable Cells |
| 1 | A1 | 4 | 2 | 0% | 8 | 21% | 0.00% |
| 2 | A2 | 2 | 1.5 | 25% | 3 | 8% | 1.97% |
| 3 | A3 | 3.5 | 2 | 5% | 7 | 18% | 0.92% |
| 4 | A4 | 2 | 4 | 3% | 8 | 21% | 0.63% |
| 5 | A5 | 1 | 0.5 | 100% | 0.5 | 1% | 1.32% |
| 6 | A6 | 2.5 | 3 | 6% | 7.5 | 20% | 1.18% |
| 7 | A7 | 2 | 2 | 4% | 4 | 11% | 0.42% |
| 8 | | | | | 0 | 0% | 0.00% |
| 9 | | | | | 0 | 0% | 0.00% |
| 10 | | | | | 0 | 0% | 0.00% |
| | | | | **Total** | **38** | **100%** | **6.45%** |

150

(56) References Cited

OTHER PUBLICATIONS

Pataer, Apar et al. "Histopathologic Response Criteria Predict Survival of Patients with Resected Lung Cancer After Neoadjuvant Chemotherapy." Journal of thoracic oncology 7.5 (2012): 825-832. Web. (Year: 2012).*

Geschwind, J-F.H. et al. (Nov.-Dec. 30, 2000). "Chemoembolization of Liver Tumor in a Rabbit Model: Assessment of Tumor Cell Death with Diffusion-Weighted MR Imaging and Histologic Analysis," Journal of Vascular and Interventional Radiology 11(10):1245-1255.

International Preliminary Report on Patentability, issued Jul. 20, 2023, for PCT Application No. PCT/US2022/013567, filed Jan. 24, 2022, 10 pages.

International Search Report and Written Opinion, mailed May 9, 2022, for PCT Application No. PCT/US2022/013567, filed Jan. 24, 2022, 12 pages.

Pataer, A. et al. (May 31, 2012). "Histopathologic Response Criteria Predict Survival of Patients with Resected Lung Cancer After Neoadjuvant Chemotherapy," Journal of Thoracic Oncology 7(5):825-832.

Dacic, S. et al. (2023, e-pub. Sep. 12, 2023). "International Association for the Study of Lung Cancer Study of Reproducibility in Assessment of Pathologic Response in Resected Lung Cancers After Neoadjuvant Therapy," Journal of Thoracic Oncology 18(10):1290-1302.

Saqi, A. et al. (2022, e-pub. Mar. 19, 2022). "Assessing Pathologic Response in Resected Lung Cancers: Current Standards, Proposal for a Novel Pathologic Response Calculator Tool, and Challenges in Practice," JTO Clinical and Research Reports 3(5):100310, 15 pages.

* cited by examiner

100

Mean % Viable Cells Calculation

| | 110 | Sample Dimensions | | | Area | | |
|---|---|---|---|---|---|---|---|
| Slide | Slide # (e.g. A1, A2, etc) | 115 Width [cm] | 120 Length [cm] | 125 % Viable cells / sample bed | 130 Width x Length | 135 Weighted | 140 Mean % Viable Cells |
| 1 | A1 | 4 | 2 | 0% | 8 | 21% | 0.00% |
| 2 | A2 | 2 | 1.5 | 25% | 3 | 8% | 1.97% |
| 3 | A3 | 3.5 | 2 | 5% | 7 | 18% | 0.92% |
| 4 | A4 | 2 | 4 | 3% | 8 | 21% | 0.63% |
| 5 | A5 | 1 | 0.5 | 100% | 0.5 | 1% | 1.32% |
| 6 | A6 | 2.5 | 3 | 6% | 7.5 | 20% | 1.18% |
| 7 | A7 | 2 | 2 | 4% | 4 | 11% | 0.42% |
| 8 | | | | | 0 | 0% | 0.00% |
| 9 | | | | | 0 | 0% | 0.00% |
| 10 | | | | | 0 | 0% | 0.00% |
| | | | | **Total** | **38** | **100%** | **6.45%** |

150

*FIG. 1*

200

202 Site Number: GDA 204 Subject Number: 14 206 Date of Assessment: 1/26/2020 208 Pathologist Name: J. Doe

| | | | Sample Dimensions | | | | | Area | | |
|---|---|---|---|---|---|---|---|---|---|---|
| 210 Block ID | 212 Slide (T) | 214 Slide # | 220 Width [cm] | 225 Length [cm] | 230 % Viable Cells / Sample | 232 % Necrosis | 234 % Stroma | 240 Width x Length | 242 Weighted | 245 Mean % Viable Cells |
| 14-1 | 1 | A1 | 4.0 | 2.0 | 0.0% | 50.0% | 50.0% | 8.00 | 0.24 | 0.00% |
| 14-1 | 2 | A2 | 2.0 | 1.5 | 25.0% | 25.0% | 50.0% | 3.00 | 0.09 | 2.22% |
| 14-1 | 3 | A3 | 3.5 | 2.0 | 5.0% | 30.0% | 65.0% | 7.00 | 0.21 | 1.04% |
| 14-1 | 4 | A4 | 2.0 | 4.0 | 3.0% | 20.0% | 77.0% | 8.00 | 0.24 | 0.71% |
| 14-1 | 5 | A5 | 1.0 | 0.5 | 100.0% | 0.0% | 0.0% | 0.50 | 0.01 | 1.48% |
| 14-1 | 6 | A6 | 2.9 | 2.5 | 6.0% | 10.0% | 84.0% | 7.25 | 0.21 | 1.29% |
| | 7 | | | | | | 100.0% | 0.00 | 0.00 | 0.00% |
| | 8 | | | | | | 100.0% | 0.00 | 0.00 | 0.00% |
| | 9 | | | | | | 100.0% | 0.00 | 0.00 | 0.00% |
| | 10 | | | | | | 100.0% | 0.00 | 0.00 | 0.00% |
| | | | | | | | 100.0% | 33.75 | 1.00 | 6.74% |

| 250 Weighted % Viable Cells | 255 Non-Weighted % Viable Cells | 260 Average % Necrosis | 265 Average % Stroma | 270 MPR Assessment |
|---|---|---|---|---|
| 6.74% | 23.2% | 22.5% | 54.3% | Yes |

*FIG. 2*

PATHOLOGICAL RESPONSE CALCULATION AND ASSESSMENT TOOL

CROSS-REFERENCE TO RELATED APPLICATIONS

This application is a continuation of International Application No. PCT/US2022/013567, filed on Jan. 24, 2022, which claims the benefit of and the priority to U.S. Provisional Application No. 63/141,377 entitled "PATHOLOGICAL RESPONSE CALCULATION AND ASSESSMENT TOOL" and filed on Jan. 25, 2021, which is hereby incorporated by reference in its entirety for all purposes.

TECHNICAL FIELD

This disclosure generally relates to tools for assessing responses of subject tissues to selected stimuli and evaluating the response thereto.

BACKGROUND

Currently, there is no established guidance on how to process and evaluate resected lung cancer specimens after neoadjuvant therapy in the setting of clinical trials and clinical practice. There is also a lack of precise definitions on the degree of pathologic response, including major pathological response (MPR) or pathological complete response (pCR). In other cancers, pathologic assessment of the effects of neoadjuvant therapy have been investigated, resulting in recommendations on how to handle these specimens. A comprehensive mapping approach to gross and histologic processing of osteosarcomas after induction therapy has been used for years. In addition, new treatment modalities, including immunotherapy and targeted molecular therapies, may change the tumor microenvironment and the manner in which specimens are scored pathologically. Various recommendations for pathologic specimen processing for neoadjuvant trials in high-risk early-stage cancers have been provided.

Some recommendations for the processing and evaluation of lung cancer resection specimens have been made, including initial identification of definitions for pathological response, including MPR and pCR. It has been proposed that these definitions can be applied to all systemic therapies, including chemotherapy, chemoradiation, molecular-targeted therapy, immunotherapy, or any future novel therapies yet to be discovered, whether administered alone or in combination. Standard pathological response assessment is expected to allow for correlations with event-free survival (EFS) and overall survival (OS) in ongoing and future trials. The International Association for the Study of Lung Cancer (IASLC) has a goal to collect such data from existing and future clinical trials. Additionally, the aforementioned recommendations included guidelines for clinical practice generally, whether in clinical trials or not, to improve the consistency of pathologic assessment of treatment response. However, even with advanced recommendations, there is a lack of computer-implemented tools and methods to be used in assessing MPR or pCR in certain types of cancers in the clinical setting and elsewhere that can be used to enforce and further facilitate the goals of consistency of evaluations and improve the overall collection of pathologic data.

SUMMARY OF PARTICULAR EMBODIMENTS

In particular embodiments, a computer-implemented method includes, for each of a set of samples, receiving data input including dimensions of a sample area, a percentage of the sample area including viable cells, and a percentage of the sample area including necrosis. In particular embodiments, the sample area can include some or all of a slide, tumor bed, sample margins, sample cassette, or other suitable method of carrying and recording samples of interest. For each of the set of samples, the computer can be programmed to compute a percentage of the sample area including stroma based on the respective percentages of the sample area including viable cells and necrosis. For each of the set of samples, the computer can be programmed to computing weighting factors. The computer can be programmed to compute a weighted percentage of the set of samples including viable cells based on the computed weighting factor and percentage of the sample area including viable cells for each of the set of samples. The computer can be further programmed to determine that a specified condition is detected in the set of samples based on the computed weighted percentage of the set of samples including viable cells satisfying a threshold correlating with an indication of the specified condition.

In particular embodiments, the computer can be further programmed to compute an average non-weighted percentage of the set of samples including viable cells and determine that the specified condition is detected in the set of samples based on the computed average non-weighted percentage of the set of samples including viable cells satisfying a second threshold correlating with the indication of the specified condition. In particular embodiments, the computer can be programmed to assess a reliability of the determination that the specified condition is detected in the set of samples based at least in part on a comparison between the computed weighted percentage of the set of samples including viable cells and the computed average non-weighted percentage of the set of samples. The set of samples can correspond to a first period of time, and the computer can determine that the specified condition is detected in a second set of samples that correspond to a second period of time based on a second computed weighted percentage of the second set of samples including viable cells satisfying the threshold correlating with the indication of the specified condition and compute a difference in weighted percentage of the set of samples including viable cells over time based on the first computed weighted percentage and the second computed weighted percentage.

In particular embodiments, the computer can compute clinical population metrics based on the weighted percentage of a plurality of sets of samples including viable cells, each set of samples corresponding to a member of the clinical population. In particular embodiments, receiving the data input includes detecting one or more sources of error in the received data input. The sources of error can include a percentage greater than 100%; missing data values; incomplete data values; dimensions of the sample area failing to satisfy a threshold sample area; or received data input values exceeding a specified range, where the specified range is based on other received data values. The computer can further, in response to detecting one or more sources of error, display a prompt to instruct an operator to correct the detected source of error. In particular embodiments, the computer can further request an operator to review the data input, computed percentage of the sample area including stroma, and weighted percentage of the set of samples including viable cells. In particular embodiments, the set of samples include a resected lung cancer tumor and the specified condition is the resected lung cancer tumor exhibiting a major pathological response to treatment.

In particular embodiments, a computer-implemented method includes, by one or more computing devices, receiving, for each of a set of samples, data input including one or more images corresponding to each sample. The one or more computing devices can, for each of the set of samples, assess the one or more images corresponding to each sample to determine dimensions of a sample area, a percentage of the sample area including viable cells, a percentage of the sample area including necrosis, and a percentage of the sample area including stroma. The one or more computing devices can, for each of the set of samples, compute weighting factors. The one or more computing devices can compute a weighted percentage of the set of samples including viable cells based on the computed weighting factor and percentage of the sample area including viable cells for each of the set of samples. The one or more computing devices can determine that a specified condition is detected in the set of samples based on the computed weighted percentage of the set of samples including viable cells satisfying a threshold correlating with an indication of the specified condition. In particular embodiments, assessing the one or more images corresponding to each sample includes applying one or more computer vision models to the one or more images. In particular embodiments, the one or more computer devices can further, prior to determining that a specified condition is detected in the set of samples, display a prompt to request an operator to review the determined percentages and one or more images.

The embodiments disclosed herein are only examples, and the scope of this disclosure is not limited to them. Particular embodiments may include all, some, or none of the components, elements, features, functions, operations, or steps of the embodiments disclosed herein. Embodiments according to the invention are in particular disclosed in the attached claims directed to a method, a storage medium, a system and a computer program product, wherein any feature mentioned in one claim category, e.g., method, can be claimed in another claim category, e.g., system, as well. The dependencies or references back in the attached claims are chosen for formal reasons only. However any subject matter resulting from a deliberate reference back to any previous claims (in particular multiple dependencies) can be claimed as well, so that any combination of claims and the features thereof are disclosed and can be claimed regardless of the dependencies chosen in the attached claims. The subject-matter which can be claimed includes not only the combinations of features as set out in the attached claims but also any other combination of features in the claims, wherein each feature mentioned in the claims can be combined with any other feature or combination of other features in the claims. Furthermore, any of the embodiments and features described or depicted herein can be claimed in a separate claim and/or in any combination with any embodiment or feature described or depicted herein or with any of the features of the attached claims.

BRIEF DESCRIPTION OF THE DRAWINGS

FIG. 1 illustrates an example embodiment of a pathological response calculation tool.

FIG. 2 illustrates an example embodiment of a pathological response calculation tool.

DESCRIPTION OF EXAMPLE EMBODIMENTS

Figure 3:
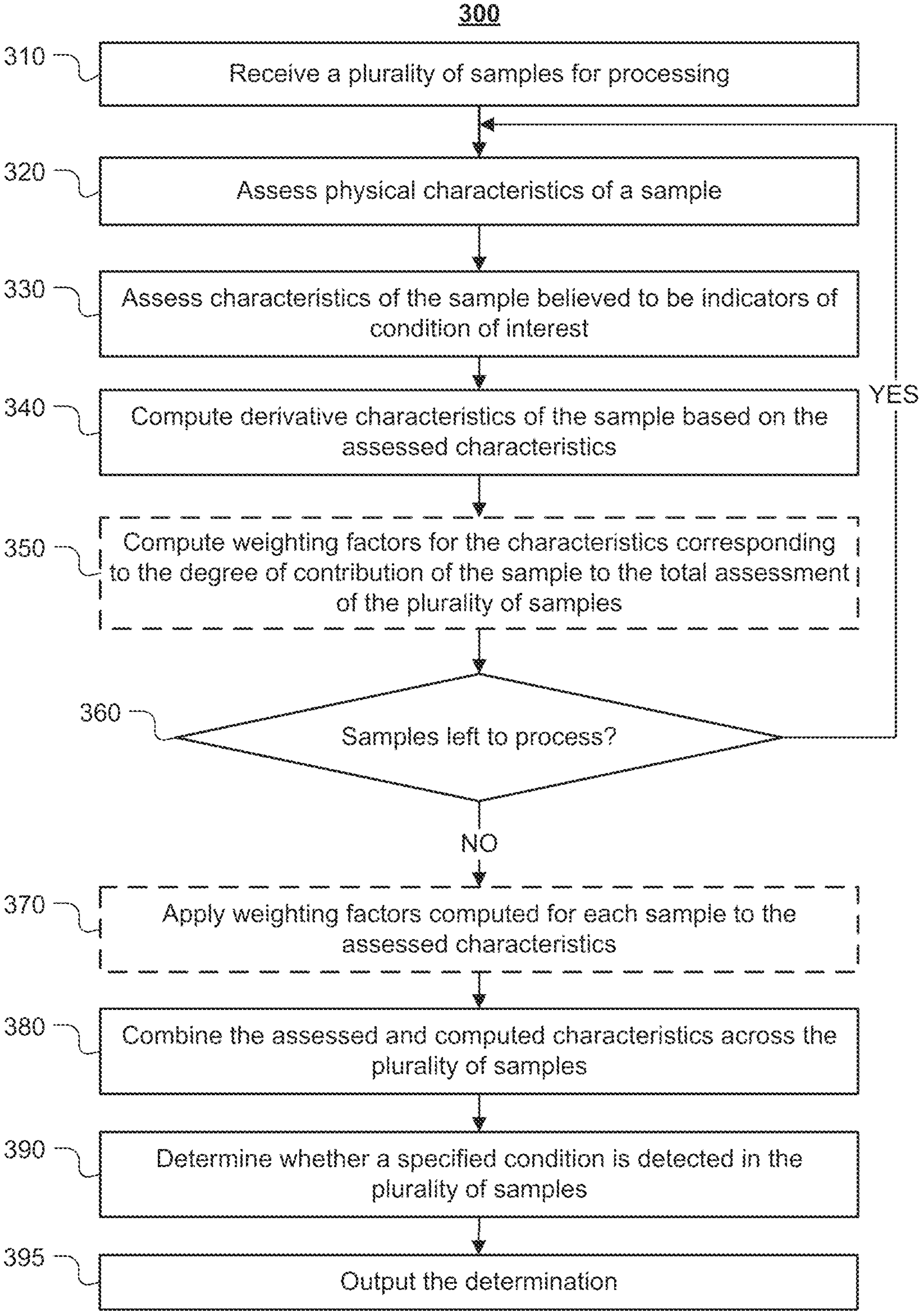
FIG. 3 illustrates an example method for determining whether a specified condition has been detected in a plurality of samples.

Standard treatment options for patients with resectable lung cancer have been settled for more than two decades. As an example, preoperative chemotherapy became a standard option when a meta-analysis of neoadjuvant chemotherapy trials reported that preoperative platinum-doublet chemotherapy improved survival over operation alone in resectable early-stage NSCLC. The magnitude of improvement of survival outcome is thought to be significant with manageable hazard ratios. Although large and lengthy adjuvant studies assessing new strategies beyond chemotherapy have to date yielded negative results, systemic therapy for advanced lung cancer has evolved such that for certain subgroups of patients, platinum-doublet chemotherapy alone has become less common in comparison to other options such as, for example, the use of tyrosine kinase inhibitors, immunotherapy alone, and chemotherapy plus checkpoint inhibitors. Conversely, there have been no changes to the standard of care in resectable disease in close to twenty years. Studies are needed to move these advances into the curative setting, which remains a high unmet need with only a 5% five-year survival benefit.

In adjuvant trials, the efficacy of the therapy cannot be determined until years later when event-free survival (EFS) or disease-free survival (DFS) and overall survival (OS) are available. DFS and OS are thus blunt tools with high potential for conflating factors and requiring considerable investment to track results over time. This necessarily delays the time before definitive results can be determined as well as the overall value of the results. Neoadjuvant trials allow efficacy end points such as clinical and pathologic response to be determined in several months. Neoadjuvant treatments offer potential advantages over adjuvant treatments, including the ability to treat micrometastatic disease and analyze the treatment-related effect on the primary tumor. Neoadjuvant treatment with surrogate measures of efficacy (e.g., surrogate endpoints) such as pathological treatment response have the potential to accelerate curative therapies for this patient population.

Currently, there is no established guidance on how to process and evaluate resected lung cancer specimens after neoadjuvant therapy in the setting of clinical trials and clinical practice. There is also a lack of precise definitions on the degree of pathologic response, including major pathologic response (MPR) or complete pathologic response (pCR), however data from retrospective and/or non-randomized single-arm studies have indicated that patients, particularly with lung cancers, that show an MPR defined as 10% or less viable tumor cells may have a significantly improved survival rate. This reporting has led to design of neoadjuvant therapy clinical trials for resectable lung cancer in which MPR is a primary endpoint due to being a quantifiable measure for evaluating results by evaluating resected samples directly.

However, even with these recommendations, there is a lack of computer-implemented tools and methods to be used in assessing MPR or pCR in certain types of cancers in the clinical setting and elsewhere that can be used to enforce and further facilitate the goals of consistency of evaluations and improve the overall collection of pathological response data. There is a noted lack of standardization for the calculation and treatment of MPR among potentially widely varying clinical studies. Even outside the realm of study of effectiveness of lung cancer treatments, there is no widespread adoption of a straightforward standardized tool for calculating MPR. In particular, each pathologist or study technician may have their own standards for using particular sample slides, scoring individual samples, and potentially weighting the contribution of each measured sample to an overall assessment of MPR for the purpose of declaring clinical results.

In particular embodiments, MPR may be calculated based on the relative amount of a tumor or other defined mass of interest contained in a given unit of a sample. As an example, a MPR can be calculated for a tumor based on an individual slide or sample of the tumor. The accuracy of MPR may be enhanced by using a larger number of measurements, for example using multiple slides for a given block of a sample. In particular, MPR can be calculated based on the amount of the tumor that can be classified as comprising or exhibiting certain conditions. For example, MPR may be used to assess the number of viable cells in a tumor bed, which may also have necrosis and stroma (which may include inflammation). In such cases, the presence and documentation of necrosis and stroma is useful to describe and distinguish complex response profiles. The amounts of the tumor can be expressed in terms of percentages, so that the total must equal to 100%. Thus, in the case of a sample of a tumor, the area of the tumor can be divided into a percentage of the tumor bed that exhibits or includes viable cells, a percentage of the tumor bed that exhibits or includes necrosis, and a percentage of the tumor bed that exhibits or includes the stroma.

From the above described percentages for each sample, an average percentage of each type of condition can be collected across the slides under analysis for a given block to determine an approximate amount of each across the block (e.g., across the resected sample). For example, where the conditions of interest include viable cells, necrosis, and stroma, an average percentage of viable cells, necrosis, and stroma can all be calculated across the block.

In certain embodiments, MPR can be evaluated by comparing the computed average value of one or more of these conditions to a predetermined threshold. The predetermined threshold can be based, for example, on the indication sought, the type of mass being evaluated, a category of the disease being evaluated, etc. For example, a block of resected sample of the tumor can be said to exhibit MPR where the average percentage of the block comprising viable tumor cells is below 10%. As this average is calculated across the number of slides, but necessarily relative to the surface area of each individual slide, this calculated can be referred to as a non-weighted average.

Additionally, or alternatively, a weighted average can be calculated using the area of each sample, such that a more accurate calculation for the percentage of the block comprising or exhibiting certain conditions can be evaluated. In this way, larger samples will contribute more to the average than smaller samples. In addition to the area of the sample, other metrics to account for the value of information provided by each slide can be used, such as by evaluating the mass of a slide relative to the block, the density of the slide relative to the block, the position in the block from which the material in the slide was taken, or other objective measures. As an example, in the case of using the area of the slide to weight the contribution of each slide to the evaluation of the block, the percentage of the block comprising or exhibiting a particular condition can be calculated as $$\sum_{i}^{n} \frac{l_i w_i}{A_b} C_i$$

where n is the number of samples, $l_i$ is the length (e.g., in cm) of the material under evaluation in slide i, $w_i$ is the width (e.g., in cm) of the material under evaluation in slide i, $A_b$ is the total area (e.g., in cm2) of all slides in block b of the sample $$\left(\text{i.e. } A_b = \sum_{i=1}^{n} l_i w_i\right),$$

and $C_i$ is value of the condition of interest for the slide i. As an example, the weighted percentage of a block comprising viable cells can be calculated as $$\sum_{i}^{n} \frac{l_i w_i}{A_b} V_i$$

where $V_i$ is the percentage of slide i comprising viable cells. In particular embodiments, it may be beneficial to compute and compare the weighted and non-weighted averages of the conditions of cells as an efficient comparison between clinically validated response mechanisms.

Persons of skill in the art will recognize that there are numerous benefits to be achieved by a tool to automatically or systematically retrieve measured values of conditions and to further automatically calculate averages of the conditions as measured (e.g., the weighted and non-weighted average percentage of a tumor bed comprising viable cells). Ultimately, the tool can be used to aid researchers in the discovery of new surrogate endpoints for overall survival rates, which, as explained herein are ultimately a difficult measure of success to use to the high likelihood of conflating factors and the oftentimes long timeframe. The automated calculation tool can assist in confirmation of suspected surrogate endpoints, and can also assist in discovering new endpoints by providing a standardized and easily-reviewed data set, which may be ripe for further analysis by human researchers or machine-learning systems.

Using an automated calculator tool such as that described herein, the data collected regarding each sample in a study can be easily standardized, with the tool acting to automatically enforce the terms of the standardization, for example to ensure that all requisite data for each sample has been collected. This can ensure that evaluators, such as different pathologists, all use the same criteria when evaluating MPR. Ensuring the same use of criteria facilitates the comparison of clinical results across studies, aiding with clinical validation. In addition, standardizing the collection and analysis of sample data can provide for more effective inter-observer comparisons, facilitating evidence-based benchmarking of pathologists evaluations even across samples. For example, two pathologists may disagree on the number of samples in a given set that exhibit a particular condition. A standardized and automated tool can simplify the procedures for identifying areas of disagreement and potentially adjudicate the true outcome. These areas of disagreement may be relatively minor, and even acceptable. such as in identifying a precise percentage of a sample area that exhibits a condition. In such cases automated tools can help pathologists in a study and the community as a whole arrive at a consensus or adjudicate an acceptable range of disagreement. Areas of disagreement may be relatively larger, however, and an automated calculation tool can help identify the areas with the largest discrepancy which may indicate further analysis and study is needed or that corrective behavior will be beneficial. Thus the automated calculation tool can serve to direct further research on what areas require better analytical techniques. As another example of the calculation tool giving direction to further research, the calculation tool can provide for simplified evaluation of whether certain types or categories of data are more useful in a clinical setting than others. For example, the calculation tool can assist in determining whether weighted averages or non-weighted averages provide more evaluative feedback or assist in determining which conditions in a given sample should be recorded. This can be used in a feedback loop to change the structure of a study, for example by providing evidence for the preferred timing, size, or number of samples collected.

Additionally, a calculation tool can improve the ease of use for pathologists, which on its own can reduce errors. Improving ease of use can also increase the rate at which pathologists can enter and manage data by improving the discovery of potential errors. The MPR calculation tool can detect likely sources of error (e.g., missing data, data demonstrating typographical errors, etc.) and avoid other sources entirely, such as mathematical errors when performing final calculations. As an example, the calculation tool can detect when a set of entered samples does not exceed an expected amount, causing the operator to re-evaluate their data entry practices and ensure that no samples have been missed. In addition, the calculation tool can review data while it is being entered or after it has been entered to look for signs of an error, such as an unreasonably large sample size, clearly incorrect values being entered, or similar. This can improve the overall quality of the data collected by reducing the instances of simple error. Performing automated review can also direct the attention of a reviewing or secondary operator to areas of apparent error, streamlining the workflows of the secondary operators.

Examples will now be discussed illustrating potential workflows that can be provided in an MPR calculation tool. Core features of the MPR calculation tool include the simple and efficient entry of data for one or more samples or slides, the automated processing of the entered data (e.g., for varying levels of data validation), the computation of statistics for the block of tissue from which the samples are taken, and a final assessment of whether a MPR has been detected.

In particular embodiments, the MPR calculation tool may be integrated with imaging technology or may display a live or captured image of a sample in a streamlined interface. Placing the image in the interface reduces the transition time for a technician evaluating the samples. However, integrated image data may not be available in all cases, thus the operator of the MPR calculation tool may look to third-party tools to evaluate the sample. As discussed herein, evaluating the sample include taken measurements of the profile of the sample, such as the size, shape, weight, density, etc. Then, based on the type of tissue being evaluated, presenting criteria for the tissue are evaluated. For example, in addition to measurement the size, weight, or density, the technician may determine an approximate oxygenation level of the tissue, a degree of exposure or production of various component, or a percentage of the visible sample area that comprises or exhibits certain cells or conditions. In one example, the technician determines the percentage of the sample area that comprises viable cells and necrosis. As used herein, the term “sample area” can be used to refer to any suitable component or subdivision of a sample under analysis, for example a suitable sample area may be dependent on the type of analysis being before. As an example, only and not by way of limitation, sample area can be used interchangeable or in conjunction with some or all of a slide, tumor bed, sample margins, sample cassette, or other suitable method of carrying and recording samples of interest. As the technician makes these determinations, the technician enters the determined values into appropriate fields. The MPR calculation tool can also calculate certain values based on the amounts entered in the other fields. After values for each sample from the tissue block are entered, the MPR calculation tool can perform one or more calculations of interest, once again based on the type of tissue being evaluated and the goals of the clinical study.

FIG. 1 illustrates an first example embodiment of a MPR calculation tool and in particular for a tool performing a calculation of a weighted percentage of entered samples comprising viable cells across all samples. In this example, the MPR calculation tool includes a table 100 with rows configured for the technician to enter data for each of several samples. The table includes a column 110 for storing an identifier for each sample. The table includes columns 115 and 120 for the width and length, respectively, of the area of a sample, in this case a resected tumor. The table includes a column 125 into which a technician enters the determined percentage of the area of the sample bed comprising viable cells. The remaining cells shown in the table are all automatically calculated and will be updated as the operator enters more sample information. Column 130 comprises a calculation of the area of each sample, based on the entered width and length. Column 135 comprises a calculation of the percentage of the total area of all entered samples for a given block represented by each identified sample. Column 140 includes a calculation of the contribution of each sample to the mean percentage of the area of the sample that includes viable cells. Thus, the value 150 is the total weighted percentage of the sample area that comprises viable cells. Although it is generally preferred to include as many sample values as possible, not all available cells for the calculation tool need to be filled for a percentage of sample area comprising viable cells to be calculated.

FIG. 2 illustrates another example embodiment of an MPR calculation tool and in particular a tool for tracking information useful in a client study session as well as additional values to characterize the collected samples. In this example, the MPR calculation tool includes a table 200 with rows configured for the technician to enter data for each of several. The MPR calculation tool includes fields such as field 202 for the recording of the clinical site where the sample was retrieved or assessment, field 204 for recording an identifier for the subject (e.g., the patient from which the sample was retrieved), field 206 for recording the data of the assessment, and field 208 for recording the name of the pathologist who performed the assessment. Combined with records from many samples, this information can be used to track the data and identify trends (e.g., determine that a given pathologist averages a higher estimation of certain cell conditions). The table includes columns for storing various types of information.

The table includes a column 210 for an identification number for the block, a column 212 for an identification number for the slide as assigned for use in the table, a column 214 for an identification number for the slide as assigned by the team or person who retrieved the sample. For example, the sample may be one of many retrieved during a surgery, and the samples may not be sequentially numbered due to samples retrieved of insufficient size, etc. The table 200 may include columns 220 and 225 for the width and length of the samples, respectively. The table 200 in includes columns for recording the conditions of interest, as assessed by the pathologist, such as a column 230 for the percentage of the sample area comprising viable cells and a column 232 for the percentage of the sample area comprising necrosis. Additionally, the table can include columns that are calculated automatically by the MPR calculation tool. For example, column 234, for the percentage of the sample area comprising stroma can be calculated automatically based on the values entered in column 230 and 232, which must add up to 100%. Similarly, column 240 comprises a calculation of the area of the sample, column 242 comprises a weighted calculation based on the percentage of the total area of the sample represented by a given sample, and column 245 comprises a contribution of each row to a calculation the weighted percentage of sample area that comprises viable cells.

The table 200 further includes a display of summary information that is useful for assessing the sample overall. Element 250 displays the calculation of the weighted percentage of the block area that comprises viable cells (calculated based on the weighting factors in column 242 and the percentage in column 230). Element 255 displays a non-weighted percentage of the sample area that comprises viable cells, based on an average of the values in column 230. Similarly, element 260 displays a non-weighted percentage of the sample area that comprises necrosis, based on an average of the values in column 232 and element 265 displays a non-weighted percentage of the sample area that comprises stroma based on an average of the values in column 234. Finally, element 270 indicates an overall assessment of whether MPR has be detected for this block based on the calculations and considered discussed herein.

In addition to manual assessment and entry of values for the MPR calculation tool, the MPR calculation tool can operate automatically using computer vision to identify and characterize samples and programming to ensure consistency of values. In addition, the entered values can be used as training data for training machine learning models to better characterize and analyze sample data. For example, rather than requiring a trained pathologist to review slides or images of slides, the slide images can be made available to a computer vision algorithm that analyzes the images. The computer vision algorithm can use image segmentation and understanding to differentiate between the various conditions within the sample area and automatically assess, for example, the dimensions of the sample. After determining the dimensions of each sample, the MPR calculation tool can automatically determine, using the computer vision and understanding modules, relative percentages of the sample area comprising viable cells, necrosis, stroma, and other conditions which may be based on the type of organ that is being studied and the tumor type. This information can be recorded for the sample automatically and saved to the clinical record for the subject without requiring human intervention.

In certain embodiments, the assessed values can be provided to an operator, such as a trained pathologist or technician, to ensure that the values appear correct. In particular embodiments, the MPR calculation tool can associate a degree of confidence with each assessment to flag certain values for review by the pathologist. For example, if the determined percentages have an associated confidence level below a threshold confidence level, the MPR calculation tool can flag the values for manual review. Once all samples for a block have been entered, and optionally once verification has been performed, the MPR calculation tool can calculate the percentages discussed herein and present a determination of indication of MPR. In addition, the calculated percentages can be shown in conjunction with the MPR assessment for review by a pathologist or other technician.

As discussed herein, in addition to storing the results of individual samples and blocks, the data stored in the MPR calculation tool can be analyzed over time (and across clinical studies) to identify ongoing trends that may prove useful for providing clinical validation for the techniques discussed herein or to simply ensure that data is consistent, especially when subject or qualitative assessments are required. For example, by recording and collecting pathologist identification information each sample assessment they make, trends can be identified in pathologist performance in assessing the true percentages or other values of interest. Additionally, the collected data can be provided in a relatively standardized format to machine-learning systems as a well-conditioned dataset to facilitate automated learning. The automated learning can be used to evaluate the usefulness of proposed surrogate endpoints as well as to propose the study of additional surrogate endpoints. Similarly, cross-referencing can be performed in which multiple pathologists assess the sample set of samples as a way of directly comparing the assessment tendencies of the pathologists. As an example, if it is determined from trend overall trend analysis that pathologist A has a 15% average assessment of the percentage of sample area that comprises necrosis than pathologist B, this information can be used when evaluating study results for clinical purposes. Similarly, two pathologists can randomly be assigned to review the sample samples to determine, for example, that pathologist B rates samples with a higher percentage of sample area comprising viable cells. The sample values, and future sample value assessments, can be adjusted accordingly. Because results are likely to be provide stronger evidence when the assessments are consistent, even between pathologists, the ability to track these trends over time is expected to lead to better clinical results.

In addition, tracking information such as block identifying information and patient identifying information be used to track and compare clinical population results across a clinical study and potentially over time. For example, if a single patient submits multiple samples over time, tracking of dates and patient identifying information can be used to study effects of time and study the progress of a mass or tissue in an individual.

Although the description given herein results to certain specific types of assessments that have been determined to be useful for certain types of cancers, the MPR calculation tool can used with a wide variety of surrogate endpoints and for evaluating a wide variety of conditions, including, but not limited to evaluation pathological response of varying degrees in many varieties of cancers affecting many types of organs. Indeed, the MPR calculation tool can be used with multiple conditions, with customized indicators that are recorded, calculated, and stored by the MPR calculation tool. For example, the MPR calculation tool can include a suite of data types to be analyzed, recorded and stored, including but not limited to area of the sample, volume of the sample (which may be extrapolated from measurements in multiple dimensions), mass of the sample, density of the sample, percentage of the sample (across one or more dimensions) comprising a type of cell or other biological entity or exhibiting a specified condition, oxygenation of the sample, and many others. Additionally, the MPR calculation tool can evaluate how the data types correlate with radiological assessments (e.g., based on CT scans). Although referred to as an MPR calculation tool or MPR calculator, the calculation tool can perform different types of response assessments and share the assessments among pathologists and diagnosticians. In using the MPR calculation tool to setup a clinical study, the architect of the study can customize the MPR calculation tool as needed, using a library of values and calculations or recording her own for the study, Therefore, the MPR calculation tool can be used as a single, unifying interface for wide variety of clinical researchers, decreasing use pick-up time with reducing operator errors due to unfamiliar tools and interfaces.

The MPR calculation tool can be compatible with a wide variety of techniques for assessing sample characteristics. In particular embodiments, the evaluations, manually by pathologists or computer-assisted, are performed on slides prepared from samples extracted from subjects. However, the MPR calculation tool can be used with other types of medical images or other tools for assessment characteristics of samples in a fixed manner. For example, the MPR calculation tool can store images or video derived from less-invasive imaging techniques including, but not limited to, CT scans, CAT scans, x-ray, PET scan, SPECT scan, MRI, ultrasound, echocardiography, echoencephalography, optical tomography, thermography, and many others. Additionally, the MPR calculation tool can be compatible with raw values taken from other types of scans.

As discussed previously, a semi- or fully-automated MPR calculation tool can facilitate quality assurance and data review operations for many types of individuals who will interact with and participate in running clinical trials, such as technicians entering data, pathologists evaluating samples, and clinical supervisors or investigators reviewing data for consistency and to further derive correlative and causative effects. As an example, an MPR calculation tool can evaluate entered data to determine whether data for a given slide or block are absent and whether such absence is likely to affect the overall MPR calculation. In cases where the MPR calculation tool is fully automated, the MPR calculation tool may determine whether data for a given sample are unable to be determined, which may indicate that a sample is insufficient or another error has occurred. In cases where the MPR calculation tool requests manual entry of data, for example from evaluation of samples that cannot be completed by computer vision tools, the MPR calculation tool can detect missing data and prompt the operator (e.g., data technician or pathologist) to ensure that all requisite data has been entered. For example, the MPR calculation tool can highlight or otherwise indicate fields in a user interface that have not been appropriately filled.

In addition to evaluating for missing data, the MPR calculation tool can evaluate the data entered for a given sample to ensure that the collected samples are in compliance with study protocols. For example, a clinical study may be designed with requirements for the size, mass, or density of individual samples. The MPR calculation tool can validate entered data to ensure that each sample meets the study criteria before advancing. As an example, a clinical study may be set up to collect samples satisfying a threshold minimum length and width as well as a threshold area of the sampled material. As the operator enters values for length and width of each sample into the MPR calculation tool, the MPR calculation tool can compare the length and width to the thresholds and also compute the area for comparison to the threshold. If the sample is determined to not satisfy the study conditions, the MPR calculation tool can provide an indication or prompt the technician to review the entered values. The technician may then avoid wasted time and effort in evaluating the sample or entering data. The MPR calculation tool can also evaluate the data entered for block compliance, for example to ensure that a sufficient number of samples have been entered for each block, to ensure that the total area or volume of the block satisfies a threshold, or other similar thresholds, and that the samples have been sufficiently reviewed. As a technician or pathologist is entering samples for a given block, the MPR calculation tool can indicate if and when a block has been associated with enough samples and whether the block as a whole satisfies any determined criteria.

As another example, particular embodiments of an MPR calculation tool can evaluate entered data to determine whether values for a given sample are unreasonable. Where values are determined to be likely to be unreasonable, (e.g., based on predetermined or automatically-learned thresholds or ranges), the MPR calculation tool can prompt the operator to correct any expected behaviors or, alternately, to confirm entry of the previous value. Furthermore, the MPR calculation tool can prevent, where possible, the entry of unreasonable values by automating calculations of derivative values. For example, where entered values include the percentage of a tumor bed comprising viable tumor cells, necrosis, and stroma, the MPR calculation tool can automatically calculate the percentage of a third category once the other two have been entered (e.g., calculate the percentage of the tumor bed comprising stroma once the percentage of the tumor bed comprising viable tumor cells and necrosis are known). Additionally or alternatively, the MPR calculation tool can evaluate for certain benchmark values based on known or expected correlations between values. For example, in a given clinical study it may be determined that samples of a given size are highly unlikely to have a certain condition present (e.g., a percentage of a tumor bed comprising necrosis greater than 80%). The MPR calculation tool can be configured for said study with this information and can detect when the unlikely condition is present. The MPR calculation tool can indicate the entry of this data as a potential error, prompting the operator to confirm the value or correct an error. Additionally, or alternatively, the MPR calculation tool can compare new sample for a particular block (e.g., a new sample associated with a particular tumor), a new block for a given subject (e.g., a new tumor under study for a particular patient), or new block data for a given study (e.g., a new tumor under study associated with a clinical study) to previously entered values and determine whether a particular value is out of an expected range of values based on the historical data. The MPR calculation tool can prompt for further analysis by the operator or can flag the new data as being of potentially high interest to a clinical researcher. By analyzing entered data and prompting for further analysis, the MPR calculation tool can ensure consistency across individual operators and even multiple operators over time. Additionally, the MPR calculation tool can support blinded review of a pathologist and automated evaluations.

As another example, particular embodiments, of an MPR calculation tool can facilitate the efficient transfer of data values between operator workstations and centralized data stores. Particular operators may have preferred user interfaces for working with certain types of data. The MPR calculation tool can be customized to that operator's needs and may further facilitate the translation of collected data between interfaces as needed by the MPR calculation tool and operators. For example, the MPR calculation tool can provide a spreadsheet-style interface for certain operators and a webform-based interface for others. The spreadsheet-style interface can update calculated values continuously as new data is entered, while the webform-based interface can require submission before results are calculated, which may provide additional time for the MPR calculation tool to review and validate submissions. Additionally, the MPR calculation tool can seamlessly communicate with one or more centralized data stores so that, once the data has been validated and approved for upload, it can be stored in a convenient location, and in a convenient format, to facilitate advanced data analysis and machine learning. Furthermore, the MPR calculation tool can provide for granular levels of access and control to data. For example, a first operator can be provided access only to data for studies in which they are involved. A second operator, with a supervisory or review role, can have access to all studies being conducted at a particular location. An administrator can, in turn, access all studies being conducted over particular timeframe. Therefore, the MPR calculation tool can be used to enforce confidentiality and protect against improper use or disclosure of subject information.

FIG. 3 illustrates an example method 300 for determining whether a specified condition, such as a pathological response, has been detected in a plurality of samples. The method may begin at step 310, where a computer-implemented MPR calculation tool receives a plurality of samples for processing. The plurality of sample may be grouped to be from a single resection or evaluation event (e.g., the entire plurality of samples is from the same master sample). The plurality of samples may, for example, be received as a set of digital images corresponding to the samples. In particular embodiments, the plurality of samples may be received at a lab for analysis by one or more pathologists.

At step 320, the physical characteristics of an individual sample are assessed. The assessment can be performed directly by the computer-implemented MPR calculation tool. For example, the physical characteristics of the individual sample can include the dimensions or weight of the sample. In particular embodiments, the physical characteristics can be assessed automatically by the computer-implemented MPR calculation tool. The physical characteristics may be provided to an operator for validation. In other embodiments, the physical characteristics may be initially provided by the operator.

At step 330, the characteristics of interest of an individual sample are assessed. The characteristics of interest can be considered the characteristics under evaluation for clinical purposes or believed to be indicators of the condition of interest. The assessment can be performed directly by the computer-implemented MPR calculation tool. Continuing the example described herein, the characteristics of interest can include relative percentages of the sample area comprising viable cells and necrosis. In particular embodiments, the characteristics are assessed automatically by the computer-implemented MPR calculation tool using the techniques described herein and may be presented to a manual operator for validation. In other embodiments, the characteristics can be assessed directly by the manual operator and entered into the computer-implemented MPR calculation tool.

As described herein, the MPR calculation tool can be used to automate many steps of accessing and evaluating samples for physical characteristics and characteristics of interest. As an example, the MPR calculation tool can be used in digital or machine-assisted pathology reviews. The MPR calculation tool can be provided as a standalone tool having components for automated assessment of samples, or may be in communication with other suites of tools that are specialized for review a particular type of samples. For example, the MPR calculation tool can access a library for assessing lung cancer tumor samples for a first workflow and access a library for assessing breast cancer tumor samples for a second workflow. In both cases, the MPR calculation tool can assist in automating review of samples, identifying areas of interesting, and determining whether further review should be recommended. As an example, in the case of evaluating lung cancer tumor samples, a computer vision module of the MPR calculation tool can be used to automatically evaluate individual samples for viable tumor cells, necrosis, and stroma. As another example, a computer vision module can be used to recognize macrophages and other biomarkers. Additionally, the MPR calculation tool can be used to generated training sets for machine learning tools by generating labelled samples and correcting errors in machine-labeled samples and evaluations by a reviewing pathologist operator.

At step 340, additional, derivative characteristics of interests of the individual sample are automatically computed by the computer-implemented MPR calculation tool. The additional characteristics can be considered derivative as they are based on the already assessed and entered values for that individual sample. Continuing from the example described herein, the derivative characteristics can include the percentage of the sample area of the individual comprising stroma, which can be computed by the computer-implemented MPR calculation tool using the percentage of the sample area comprising viable cells and necrosis. At step 350, the computer-implemented MPR calculation tool may optionally compute weighting factors for the characteristics that have been assessed. The weighting factors may be selected and determined to correspond to the degree of contribution of the individual sample to the total assessment of the plurality of samples (e.g., the master sample). In the example described above, the weighting factors are based on the area of the individual sample relative to the total sample area of the plurality of samples. Other methods of determining a weighting factor can also be used.

At step 360, the computer-implemented MPR calculation tool, or manual operator, can determine whether there are additional samples of the plurality of samples yet to be processed. If so, the method returns to step 320 to process additional samples. If there are no more samples to be processed, the method proceeds to step 370.

At step 370, if weighing factors were computed, the computer-implemented MPR calculation tool applies the weighting factors computed for each sample to the assessed characteristics of each sample. For example, the weighting factors can comprise scaling factors that may be applied to one or more of the characteristics of interest before they are combined. At step 380, the computer-implemented MPR calculation tool combines the assessed and computed characteristics across the plurality of samples. As example, the assessed and computed characteristics can be combined in a weighted combination (e.g., based on the determined weighing factors). Additionally or alternatively, the assessed and computed characteristics can be combined by averaging the values of each characteristic across the plurality of samples. At step 390, based on the combined assessments, the computer-implemented MPR calculation tool determines whether a specified condition has been detected in the plurality of samples. As an example, the determination can be based on whether one or more of the combined characteristics satisfy a certain threshold. The threshold may be set based on, for example, the amount or quality of the samples, the physical characteristics of the samples, or the type of condition being assessed. At step 395, the computer-implemented MPR calculation tool outputs the determination of whether the specified condition has been detected for display and may optionally output one or more of the assessed and computed characteristics.

Although not illustrated in FIG. 3, at suitable points throughout the method 300, the computer-implemented MPR calculation tool can prompt for validation of entered values or values assessed or computed by the MPR calculation tool. As an example, after step 330, the MPR calculation tool can compare the assessed values associated with the characteristics of interest to a historical record of valid values to determine whether there is a likelihood of a value being incorrect or requiring further analysis. If a likelihood of an incorrect value is suitably high, the MPR calculation tool can even interrupt the processing of a sample to request confirmation or a secondary review. The assessment can be made based on both mathematical limits of certain values (e.g., a measurement of a portion of a sample cannot exceed the same measurement for the entirety of the sample, a percentage cannot be greater than 100%) and predetermined ranges that correlate past observations with current observations, where the ranges may be learned by the MPR calculation tool itself.

Particular embodiments may repeat one or more steps of the method of FIG. 3, where appropriate. Although this disclosure describes and illustrates particular steps of the method of FIG. 3 as occurring in a particular order, this disclosure contemplates any suitable steps of the method of FIG. 3 occurring in any suitable order. Moreover, although this disclosure describes and illustrates an example method for determining whether a specified condition, such as a pathological response, has been detected in a plurality of samples including the particular steps of the method of FIG. 3, this disclosure contemplates any suitable method for determining whether a specified condition, such as a pathological response, has been detected in a plurality of samples including any suitable steps, which may include all, some, or none of the steps of the method of FIG. 3, where appropriate. Furthermore, although this disclosure describes and illustrates particular components, devices, or systems carrying out particular steps of the method of FIG. 3, this disclosure contemplates any suitable combination of any suitable components, devices, or systems carrying out any suitable steps of the method of FIG. 3.

Figure 4:
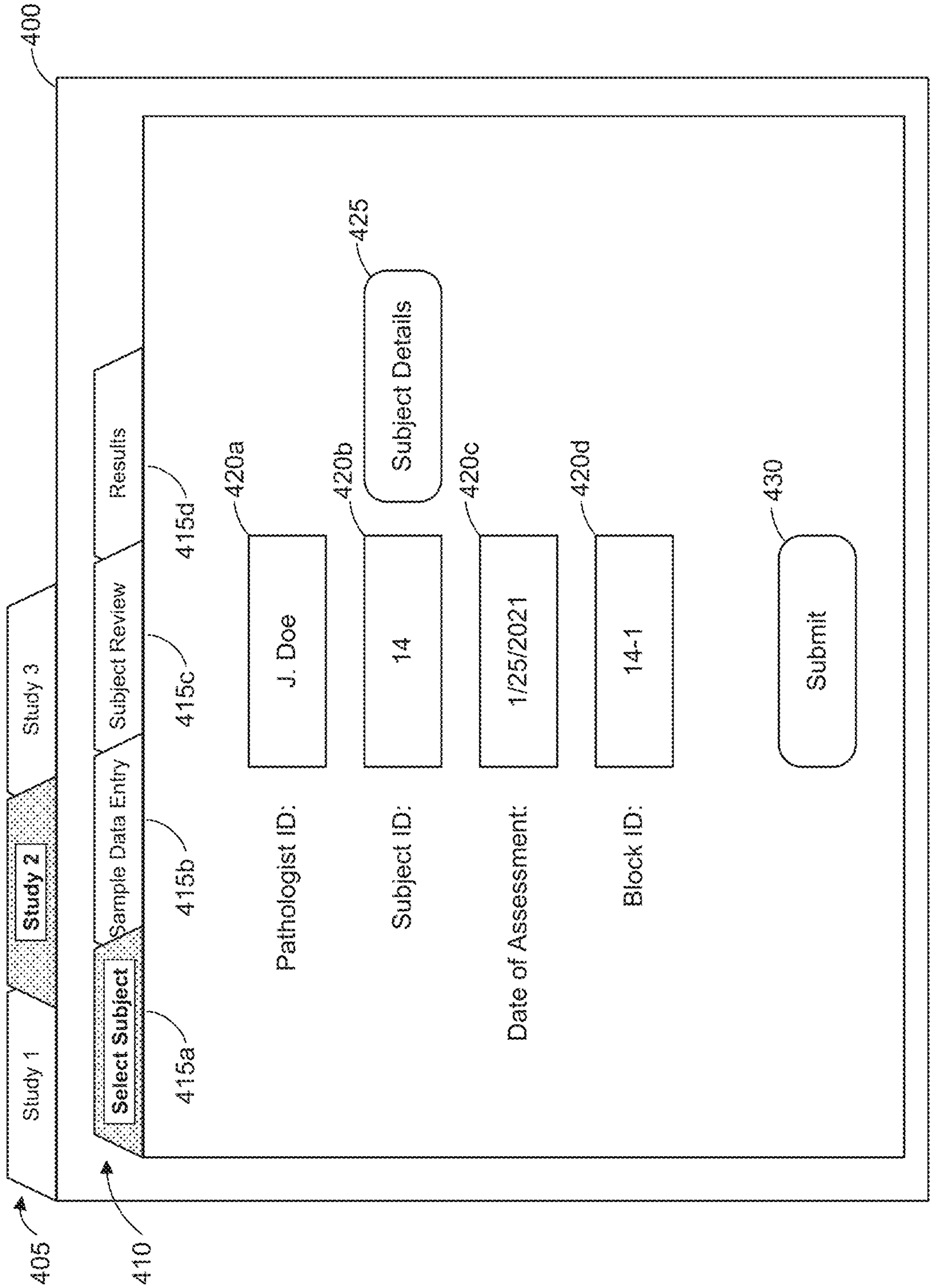
FIG. 4 illustrates an example interface of an interactive pathological response calculation tool.

FIGS. 4-11 illustrate example graphical user interfaces for an MPR calculation tool. FIG. 4 illustrates an example interface for entering data regarding sample collection. The MPR calculation tool can be used to quickly access information for multiple clinical studies simultaneously. As an example, the interface 400 can include a series of interactive elements, styled like a set of tabs 405 to facilitate a user navigating amongst the various studies for which the user can enter or review information. The interface also includes a second set of tabs 410 to facilitate the user moving between stages of data collection and entry for the MPR calculation tool. As discussed herein, the set of tabs can include a tab 415*a* corresponding to selecting a subject for which to enter information, a tab 415*b* corresponding to entering sample data for the subject, a tab 415*c* corresponding to reviewing all entered data for the sample, and a tab 415*d* corresponding to reviewing the results of the MPR calculation tool. According to particular embodiments, the display of specific tabs can be customized to allow for multiple tabs to be viewed simultaneously. For example, an operator can customize their view to show the interface corresponding to the "Sample Data Entry" tab 415*b* and the "Subject Review" 415*c* tab or "Results" tab 415*d* simultaneously or in one or more interface windows. Data entered in the "Sample Data Entry" tab 415*b* interface can be propagated throughout the result of the displayed windows. As also discussed herein, the set of tabs can include several optional tabs that define or augment the workflow of the operator and reviewer (e.g., primary pathology and second pathologist, data technician and primary investigator, etc.). In the interface 400, the tabs can be highlighted to indicate to the operator at a glance which stage of the MPR calculation process they are currently in.

Upon launching the MPR calculation tool, or upon interacting with the "Select Subject" tab 415*a* (e.g., by click, tapping, or otherwise interacting with the tab on the user interface 400), the operator is shown a series of interactive fields 420*a*-420*d* with corresponding labels as well as several interactive elements 425 and 430. As an example, interactive field 420*a* can be used to enter the name of the pathologist currently using the MPR calculation tool. Additionally or alternatively, the user may merely be responsible for entering data and not for assessing the individual samples, in which case the user can enter the name of the pathologist who made the assessment. Interactive field 420*b* can be used to enter an identifier for the subject for which data will be later entered into the MPR calculation tool. Interactive field 420*c* can be used to enter the data of the assessment of the data that will be entered into the MPR calculation tool. Interactive field 420*d* can be used to enter an identifier for the sample or block for which data will be entered. For example, if the entered block ID corresponds to a new block, the MPR calculation tool can create a new record for the data. If the entered block ID corresponds to an existing block, the MPR calculation tool can confirm that the operator wishes to change the data stored for the existing block before proceeding. The operator can select the interactive element 430 (e.g., button) to submit the information entered in the fields 420*a*-420*d* and advance to the next stage of the data entry workflow.

Figure 5:
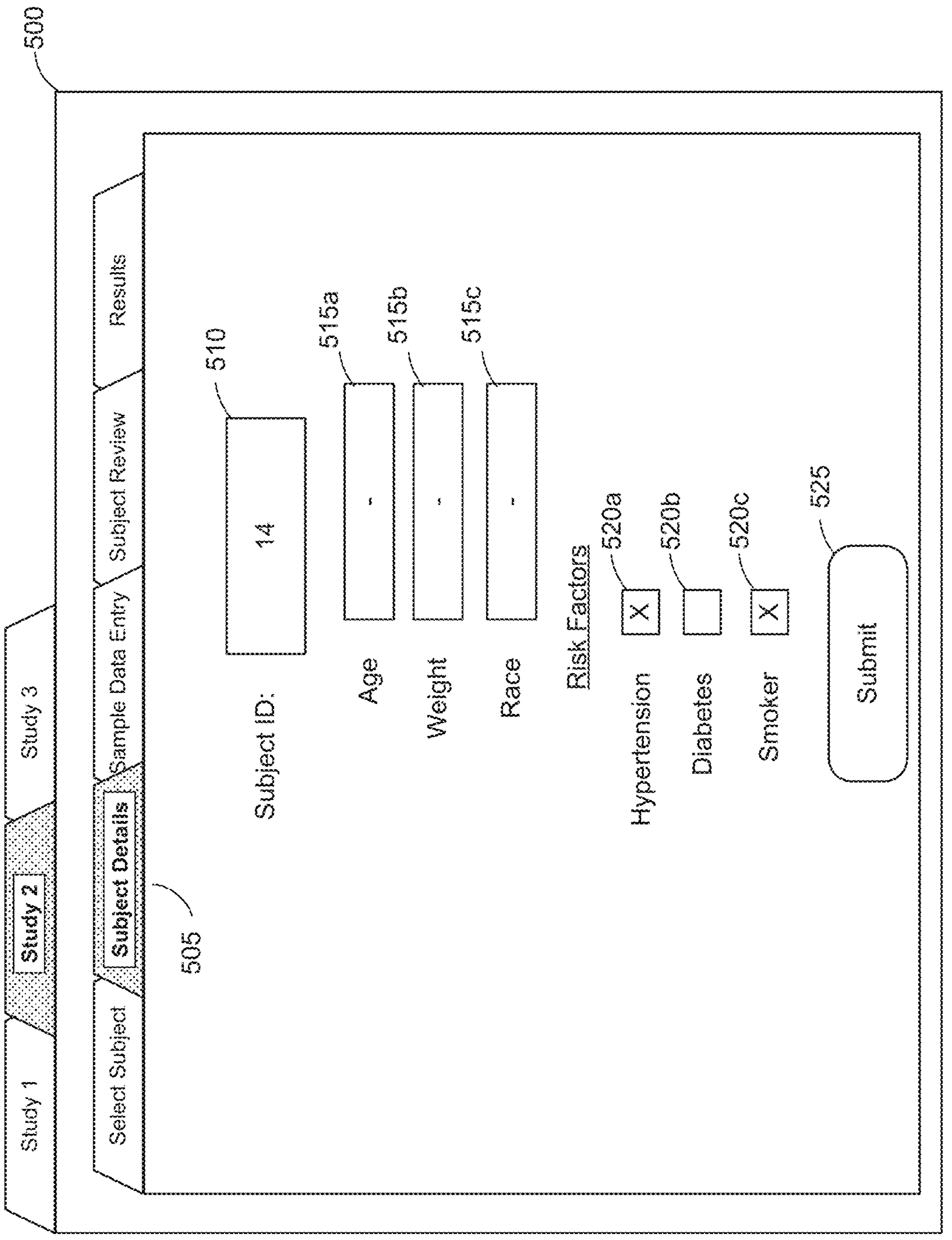
FIG. 5 illustrates an example interface of an interactive pathological response calculation tool.

Additionally, or alternatively, the operator can select the interactive element 425 to advance to an optional stage of the data entry workflow illustrated in FIG. 5. FIG. 5 illustrates an example interface 500 for entering additional details about the subject for which data is being entered by the operator. In addition to the tabs discussed with respect to FIG. 4, the interface 500 includes an additional "Subject Details" tab 505. In particular embodiments, the "Subject Details" tab may be shown next to the "Select Subject" tab 415*a* initially or may only appear once an operator interacts with the interactive element 425. The interface 500 corresponding to the "Subject Details" tab can used to collect information that can be used by researchers to perform a deeper analysis of the results, for example to determine whether confounding facts affect the calculation of MPR for the specific condition of the subject. The information entered through the interface 500 for the "Subject Details" tab 505 can be used to evaluate, for example, patient history and adverse reactions to a treatment.

In the example interface 500 shown in FIG. 5, the sample is a block of tissue taken from an individual and the interface corresponds to collecting demographic and risk factor information for the individual. Element 510 shows the subject identifier, pre-filled from information entered in the interface 400 corresponding to the "Select Subject" tab 415*a*. Interactive elements 515*a*-515*c* are fields through which the operator can enter freeform information, such as the age, weight, race of the subject, ethnicity of the subject, occupation, or other demographic information for the subject. Interactive elements 520*a*-520*c* are check box elements, through which an operator can provide a positive or negative indication of the condition for the subject if known. The conditions can be customized by the designer of the study based on known or suspected risk factors that may influence MPR calculations and outcomes. Once the operator enters the relevant information, the operator can select the interactive element 525 to save the additional details and either return to the interface 400 corresponding to the "Select Subject" tab 415*a* or advance to the next stage of the data entry workflow.

Figure 6:
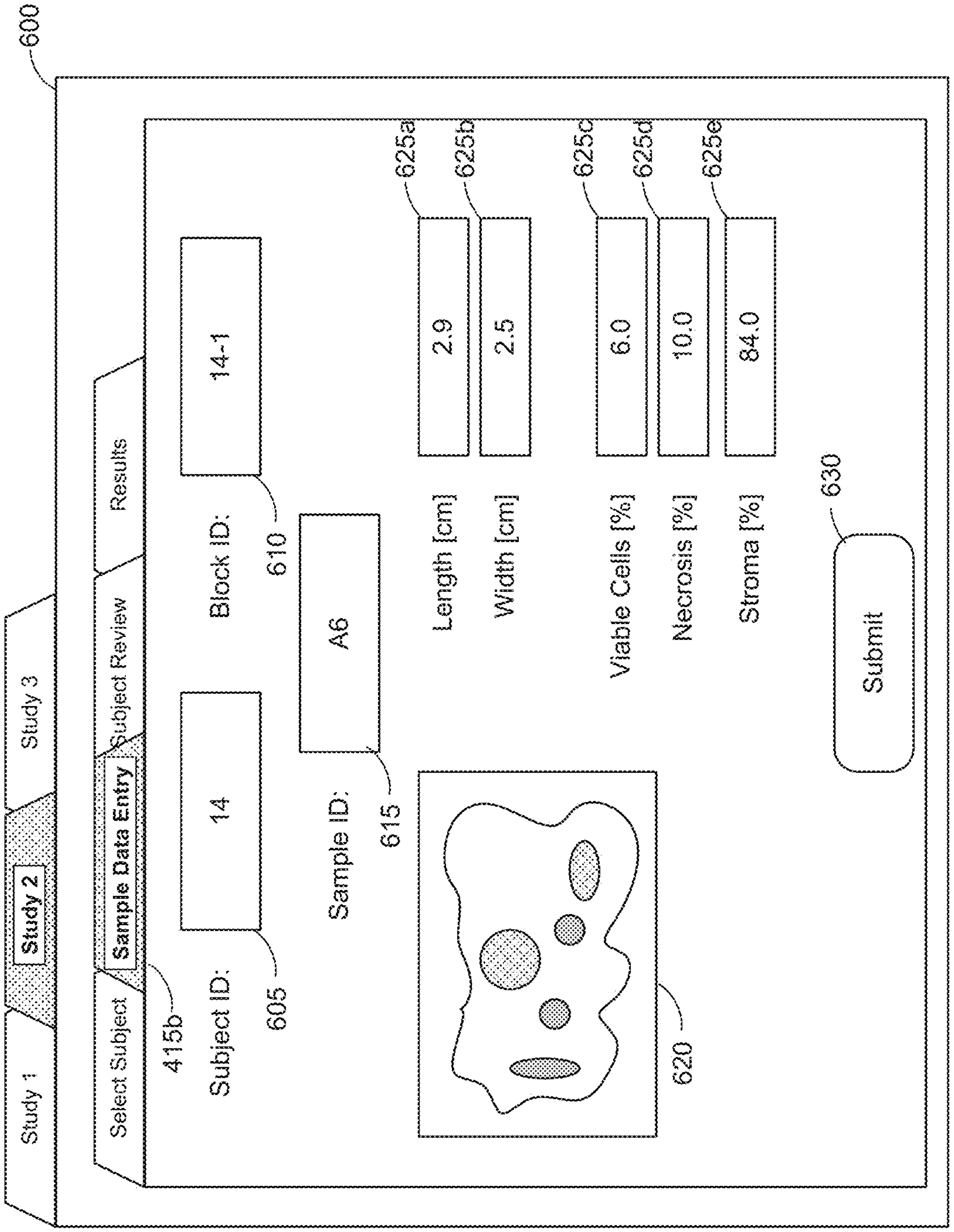
FIG. 6 illustrates an example interface of an interactive pathological response calculation tool.

FIG. 6 illustrates an example interface 600 for the next stage of the MPR calculation tool data collect workflow, corresponding to the "Sample Data Entry" tab 415*b*. The interface 600 can includes a series of interactive fields enabling the operator to enter and verify the key data for the sample needed for MPR evaluation. The example interface 600 illustrated in FIG. 6, includes the field 605 that shows the subject identifier and a field 610 that shows the block identifier, which were both entered in the interface 400 corresponding to the "Select Subject" tab 415*a*. Interactive field 615 is a text field allowing the operator to enter a sample identifier for the sample for which they are entering or verifying the rest of the data to be entered. In some embodiments, the sample identifier may be assigned at an earlier time to correlate the information from a block with other uses. For example, where the block corresponds to a portion of resected tissue (e.g., of a tumor) the sample identifier may have been assigned by the surgeon who removed the tissue or by another technician. In other embodiments, the sample identifier may be assigned by the MPR calculation tool to ensure that unique values for each sample are entered.

The interface 600 can include an element 620 showing one or more images of the sample under evaluation for which data is being entered or verified. As an example, where the sample is taken from a block of resected tissue, the image may be a digital image of a slide used to evaluate the tissue. As another example, where the sample is taken using medical imaging technology (e.g., a CT scan, PET scan, MRI, x-ray, etc.), the image 620 may be a digital image of said scan. The operator 620 can select the image 620 to zoom in on the image or view the image in a larger size or higher resolution (e.g., where the displayed image 620 is initial a thumbnail). In particular embodiments, the image 620 can be used by the operator to evaluate the sample prior to entering other data, to verify that the data corresponds to the correct sample, to confirm that the data is appropriate for the sample (e.g., to approximate the values where the sample has been evaluated by a computer vision component of the MPR calculation tool or to where the sample has been evaluated by another individual). Interactive elements 625*a*-625*e* include various fields for entering or reviewing the data corresponding to the sample indicated by the sample identifier 615. As an example, interactive field 625*a* allows the operator to enter or review the length of the sample, interactive field 625*b* allows the operator to enter or review the width of the field, interactive field 625*c* allows the operator to enter or review the percentage of the area of the sample corresponding to viable cells, interactive field 625*d* allows the operator to enter or review the percentage of the area of the sample corresponding to necrosis, and interactive field 625*e* allows the operator to enter or review the percentage of the area of the sample corresponding to stroma. As discussed herein, these values can be entered manually by the operator (based on their own evaluation or by another individual) or can be generated automatically by the MPR calculation tool using, for example, one or more computer vision and machine learning models configured to interpret digital medical imaging data and produce results of the sort required in fields 625*a*-625*e*.

In particular embodiments, one or more of the fields can be calculated automatically based on the rest of the entered values and added to the respective field for review by the operator. As an example, the MPR calculated tool can enforce the total percentage of area of the sample comprising viable cells, necrosis, and stroma being equal to 100%. Therefore, after two of these values are entered (e.g., the percentage comprising viable cells and the percentage comprising necrosis), the value for the remaining percentage can be calculated automatically, as discussed herein. In this case, the operator can review the calculated values before submission.

Once the user has entered or reviewed the values for this sample, interactive element 630 may be selected to save these results and submit them to the MPR calculation tool. In particular embodiments, after submitting the information, the operator can be prompted whether they would like to add data for an additional sample or whether they would like to review what has been submitted. In some embodiments, the interface 600 can include additional interactive elements to allow the user to specify whether they would like to enter additional data or to review the all submitted data for the block without requiring an additional prompt.

Figure 7:
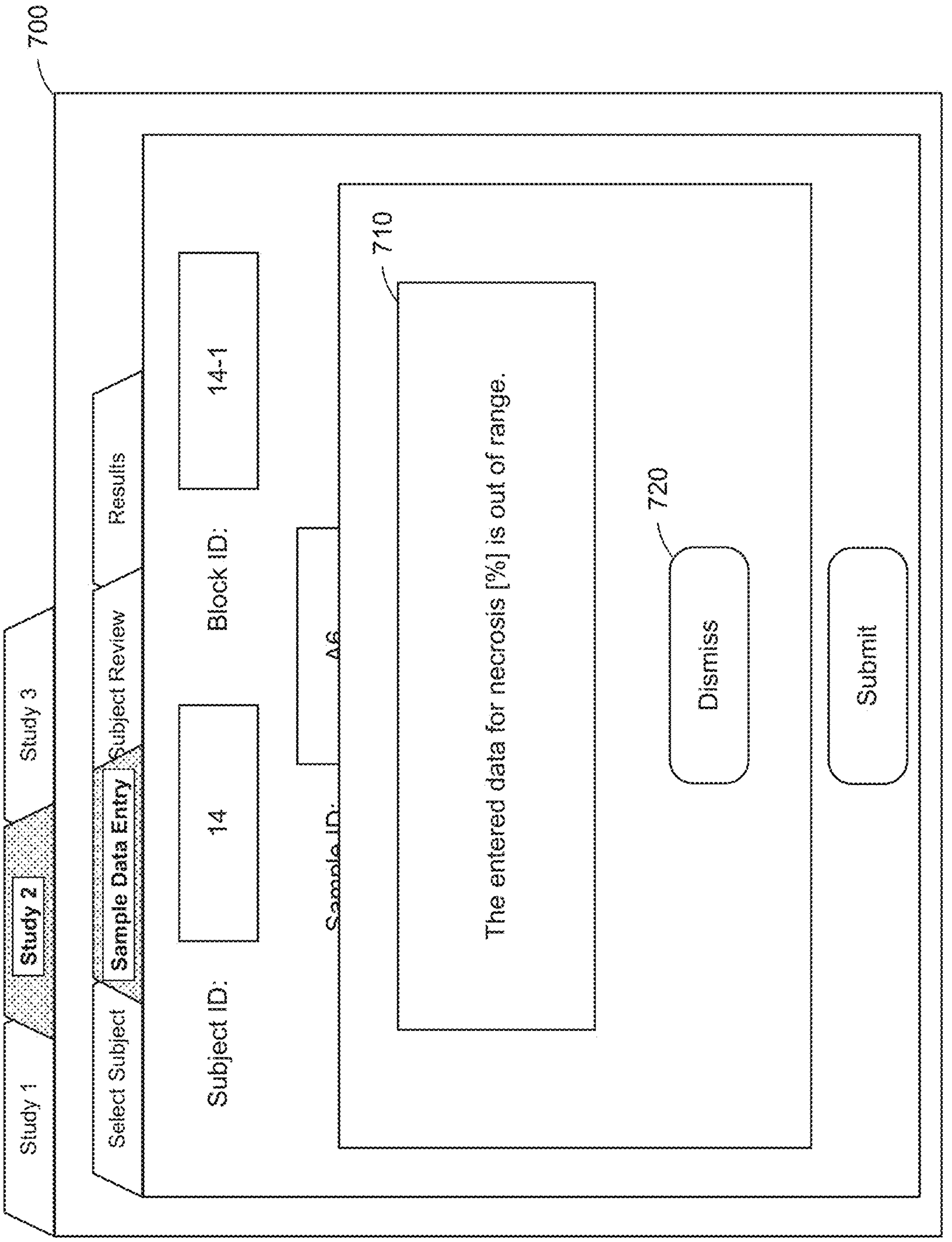
FIG. 7 illustrates an example interface of an interactive pathological response calculation tool.

As illustrated in FIG. 7, the MPR calculation tool can review the submitted data for compliance with various checks and requirements and display an interface 700 upon determining a likely error. In one embodiment, the MPR calculation tool and evaluate data after the operator has elected to submit the data for storage by the MPR calculation tool. As this, point, the MPR calculation tool can compare the entered values for completeness such as to ensure there are no blank fields that are designated as required for the clinical study. The MPR calculation tool can compare the entered values for reasonableness such as to assure that values have the correct absolute values (e.g., total percentages are not negative, measurements of dimensions are not negative) or to assure that the values satisfy pre-specified thresholds. For example, the designer of the clinical study can customize required minimum values for some of the data being entered, such as the dimensions or total area of a sample, to ensure that the samples will useful. Once the user submits the data, the values are compared against all specified threshold and checks. If an error is detected, the operator can be shown a pop-up interface element 710 explaining that an error has been detected and another interactive element 720 to dismiss the pop-up interface element 710 so that they can correct any errors. Additionally or alternatively, the MPR calculation tool can compare the values to thresholds based on other entered values. For example, based on customizations performed by the designer of the clinical study, the MPR calculation tool can calculate when the area of a sample satisfies a threshold and evaluate the percentage of necrosis based on a previous determination that the percentage should be within a particular range. If the entered value does not fall within that range, the MPR calculation tool can notify the operator that they have entered outlier values so that they can confirm the entered data is correct or return to the interface 600 and revise the entered data as needed.

In addition to a separate or pop-up alert after the user has submitted data determined to contain an error of some kind, the MPR calculation tool can review the data as the operator is entering it into the interface 600. The MPR calculation tool can detect, for example, when sample data does not comply with requirements of the clinical study or appear to contain missing or mis-typed data. In response, the MPR calculation tool can alert the operator by highlighting the entered data, displaying it in a different color, adding additional text to the interface 600 drawing attention to and explaining the nature of the detect error, or using other techniques to seamlessly alert the operator that an error has occurred. Alerting the operator in this manner can facilitate the user to quickly and accurately enter the data without the operator needing to formally submit the data before they can validate it.

Figure 8:
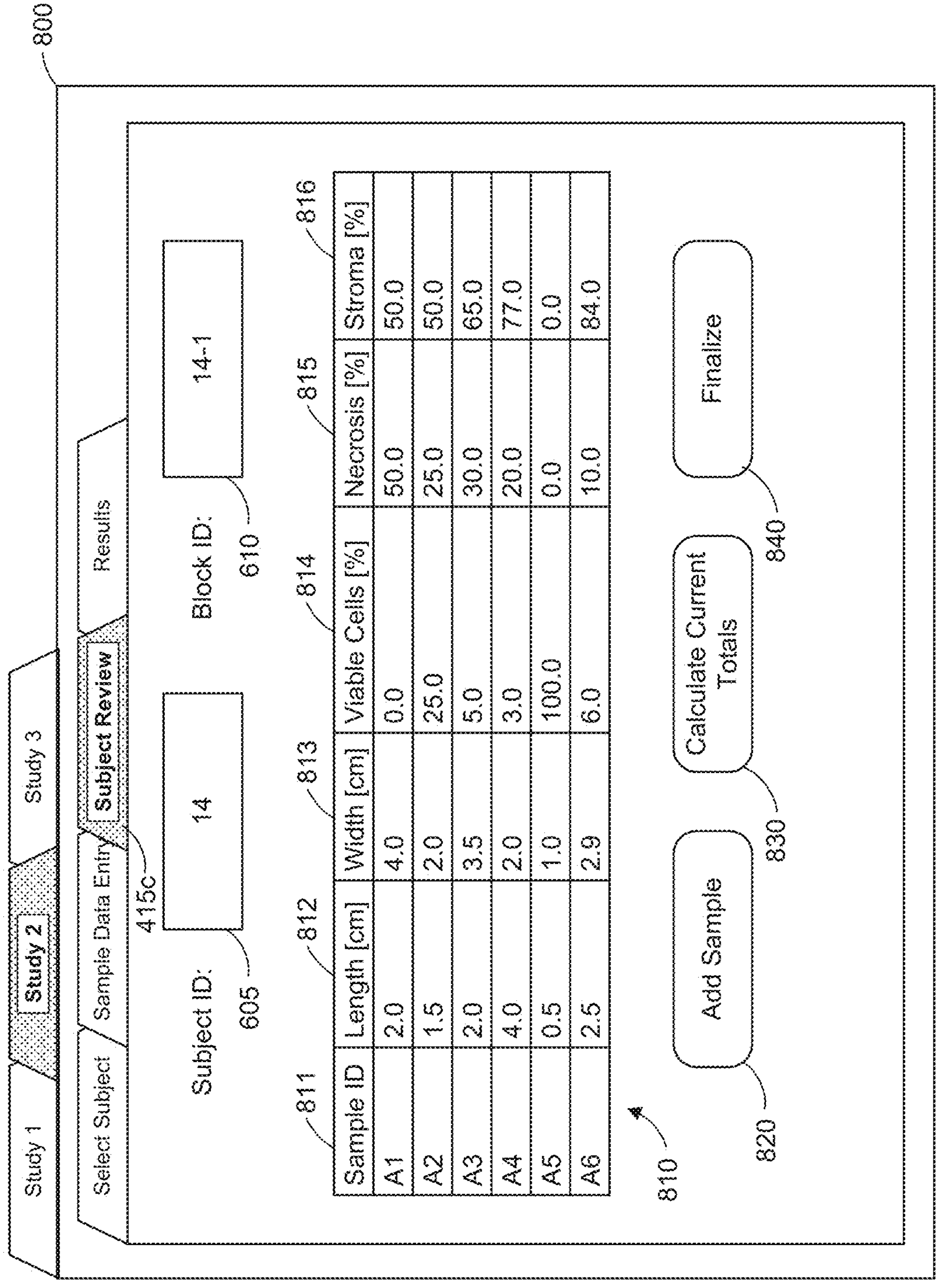
FIG. 8 illustrates an example interface of an interactive pathological response calculation tool.

After the user has entered valid data and either automatically or manually advanced to the next stage of the MPR calculation tool workflow, the MPR calculation tool can display the interface 800 illustrated in FIG. 8. FIG. 8 illustrates an example interface 800 corresponding to the "Subject Review" tab 415*c* for efficiently reviewing all entered data for the block. As with interface 600, the interface 800 corresponding to the "Subject Review" tab 415*c* includes the field 605 that shows the subject identifier and a field 610 that shows the block identifier, which were both entered in the interface 400 corresponding to the "Select Subject" tab 415*a*. The interface 800 includes a table 810 that displays all of the values entered for the samples submitted by the operator (or calculated by the MPR calculation tool and approved by the operator) for the block identified in by the displayed block identifier in field 610. The table 810 as illustrated, includes a row for each submitted sample, a column 811 for identifying the sample identifier, and columns 812-816 corresponding to the data collected for the various samples. In the example interface 800 illustrated in FIG. 8, the columns include a column 812 for sample length, a column 813 for sample width, a column 814 for the percentage of the area of the sample comprising viable cells, a column 815 for the percentage of the area of the sample comprising necrosis, and a column 816 for the percentage of the area of the sample comprising stroma. In particular embodiments, the operator can interact with a cell in the table to revise a value (e.g., to modify the length entered for a given sample). Additionally or alternatively, the operator can interact with a row to cause the MPR calculation tool to display the interface 600 corresponding to the "Sample Data Entry" tab 415*b* to review the sample (including the sample image) and potentially revise the submitted data.

The interface 800 further includes a series of interactive elements providing additional functionality. Upon selecting interactive element 820, the MPR calculation tool can transition to the interface 600 corresponding to the "Sample Data Entry" tab 415*b* for a new sample. Therefore, the interactive element 820 can be used to submit additional samples data. Upon selecting the interactive element 830, the MPR calculation tool can calculate running totals and/or averages for the data submitted for the identified block so far. The MPR calculation tool can display the calculated totals and averages in a new row of the table 810, in a pop-up interactive element, or in another interface of the MPR calculation tool. Upon selecting interactive element 840, the MPR calculation tool can transition to the final stage of the sample data entry workflow for the MPR calculation tool, where the operator can review the calculated totals and submit the final results to the study record.

Figure 9:
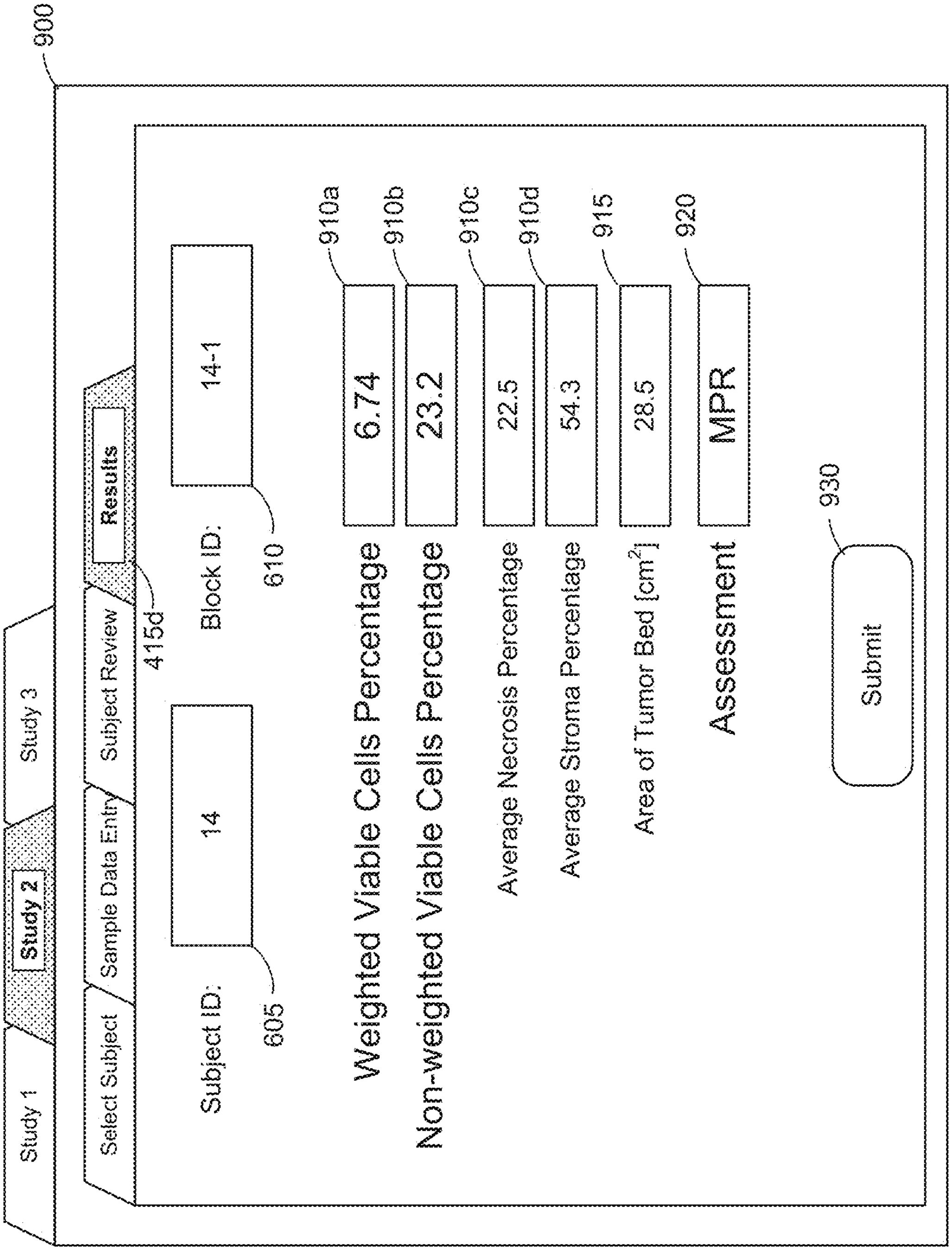
FIG. 9 illustrates an example interface of an interactive pathological response calculation tool.

FIG. 9 illustrates an example interface 900 for displaying calculated totals and reviewing MPR calculation results before information corresponding to a block is submitted to the study record. The interface 900 therefore corresponds to the "Results" tab 415*d*. As with interface 600, the interface 800 corresponding to the "Subject Review" tab 415*c* includes the field 605 that shows the subject identifier and a field 610 that shows the block identifier, which were both entered in the interface 400 corresponding to the "Select Subject" tab 415*a*. The interface also displays the totals of interest for the block, which can be customized by the designer of the clinical study. As an example, the interface 900 illustrated in FIG. 9 includes a field 910*a* to display the weighted percentage of the area of the samples submitted for the block that comprise viable cells, a field 910*b* to display the non-weighted percentage of the samples submitted for the block that comprise viable cells, a field 910*c* to display the average percentage of the samples submitted for the block that comprise necrosis, a field 910*d* to display the average percentage of the samples submitted for the block that comprise stroma, and a field 915 to display the total assessed area of the sample area. The values are all automatically calculated by the MPR calculation tool based on the data submitted or reviewed and approved by the operator. Additionally, the results reporting interface 900 can include additional fields that may be customized for the particular study or operator. For example, the reporting interface 900 can include fields to display the size of the sample area (e.g, tumor bed) at other points in time (e.g., pre-therapy, post-therapy), display an approximate percentage of the total mass examined, display the weighted and non-weighted percentages of other assessed or computed values (e.g., necrosis or stroma), etc.

The interface 900 also includes a field 920 that displays the assessment of the MPR calculation tool. The field 920 can include a simple yes or no determination for a particular type of result (e.g., whether MPR has been detected), which can enhance the usability of the MPR calculation tool (e.g., for diagnostic or evaluative purposes in addition to clinical studies). As another example, the field 920 can include a determination and listing of whether one of a set of conditions have been detected (e.g., MPR, pCR, or other, etc.). As discussed herein the condition being evaluated for and the calculation of MPR can be based on whether one or more of the calculated values (or a combination therefore) satisfies a threshold that can be set by the designer of the clinical study and which may be vary based on the type of samples being evaluated. The assessment performed may be determined by the MPR calculation tool itself based on other entered values. The interface 900 also includes an interactive element 930 for the operator to submit the final values to the study record. At any point before the operator submits the final values, the operator can easily move between the stages of the workflow by simply interacting with any of the set of tabs 410, which also indicate where in in the workflow the current interface being displayed is situated.

In addition to the interfaces discussed previously, the MPR calculation tool can comprise interfaces facilitating review of submit data by a second operator. As an example, the second operator can be another pathology whose responsibility is to confirm that entered data is reasonable and correct. The second operator can be a study lead reviewing the data before it is compiled. The second operator can also simply be another reviewer of the data. To assist the second operator in reviewing the submitted data, the MPR calculation tool and can include one or more interfaces directed to a prioritized review workflow that highlights and directs the second operator to data that the MPR calculation tool has flagged as potentially include incorrect data, outliers, or other data of interest. The prioritized review workflow may be adaptive, directing the second operator review in a sequence of view based on a learned or crowd-sourced prioritization of detected anomalies or possible errors.

Figure 10:
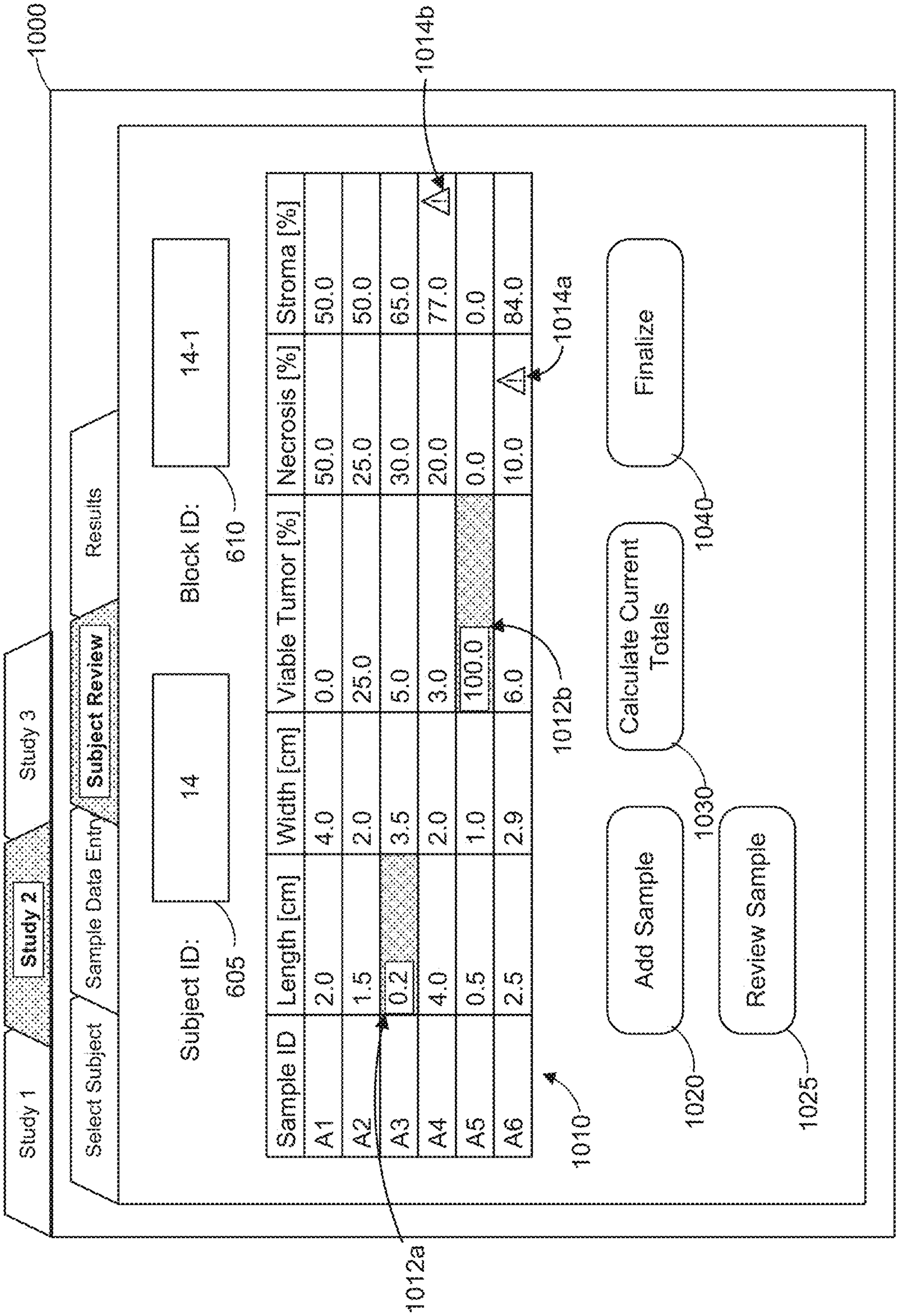
FIG. 10 illustrates an example interface of an interactive pathological response calculation tool.

FIG. 10 illustrates an example interface 1000 for prioritized review of submitted data for an individual block. Similar to interface 800, the interface 1000 for prioritized review includes field 605 for the subject identifier and field 610 for the block identifier. Interface 1000 includes a table 1010 comprising the data submitted by the first operator for the identified block. In the table, the MPR calculation tool can indicate that one or more cells contains data that has been determined by the MPR calculation tool to contain data that requires review. The data may require review for a variety of reasons discussed herein, including that the data fails to satisfy a threshold, required value, that the data includes statistical outliers or otherwise unlikely values, that the data missing a value, etc. The MPR calculation tool can indicate that the data should be reviewed in a variety of ways. For example, MPR calculation tool can highlight the cells (e.g., shown for cells 1012*a* and 1012*b*) to draw the attention of the second operator. The MPR calculation tool can also include another visual indicator, such as the symbol appending to cells (1014*a* and 1014*b*). The MPR calculation tool can use different indications to indicate, for example, different types of detected errors, to differentiate between errors that render the data unusable and other types of errors, to indicate when the cell contains a value that has been modified by the MPR calculation tool (e.g., if the MPR calculation tool corrects a suspected clerical error or supplements the provided data with information provided by an artificial intelligence component). The second operator can hover over a highlighted or otherwise designate cells to be shown an pop-up element explaining the nature of the suspected or determine error, review potential solutions to correct the problem, or potentially instructed the MPR calculation tool on how to apply the solution. Additionally, the prioritized review workflow can highlight when calculated values differ in a significant manner. For example, the MPR calculation tool can highlight or otherwise draw attention to samples where, for example, the weighted and non-weighted values of a particular condition (such as the percentage of a sample area that comprises viable cells) differ by an amount that exceeds a predetermined or learned threshold or different by an amount that may affect the clinical assessment of the sample.

Interface 1000 also interface a number of interactive elements, such as interactive element 1020 for adding a new sample (e.g., through the interface 600 corresponding to the "Sample Data Entry" tab 415*b*), interactive element 1030 for calculating the current running totals for the block based on the submitted sample data, and interactive element 1040 for re-finalizing the submitted data. Interface 1000 also includes an interactive element 1025 that, when selected by the second operator, facilitates the second operator reviewer a sample selected in the table 1010 in more detail (e.g., by transitioning to the interface 600 corresponding to the "Sample Data Entry" tab 415*b* populated with the data collected for the sample. The second operator can also perform that operation by interacting with the sample in the table 1010.

Figure 11:
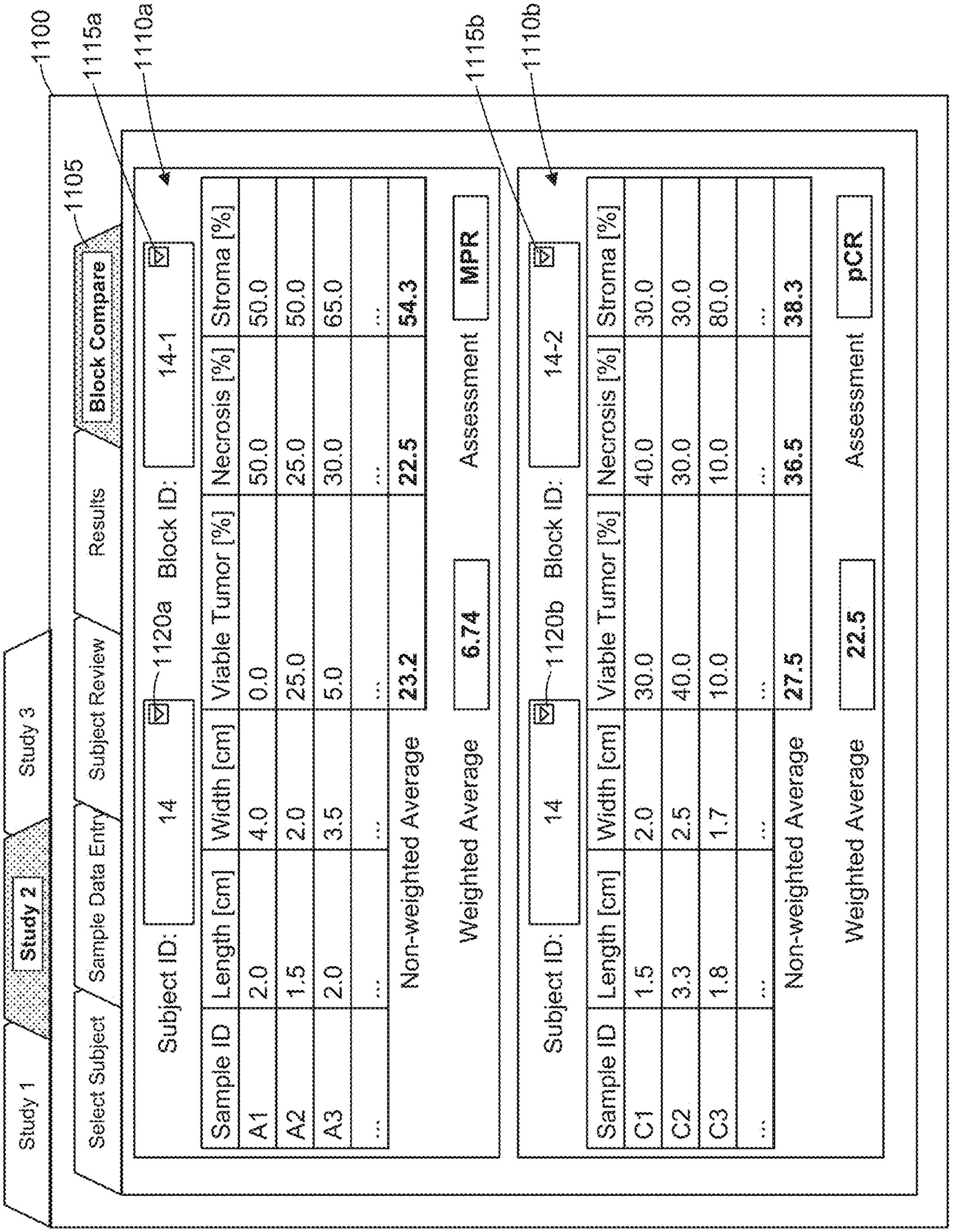
FIG. 11 illustrates an example interface of an interactive pathological response calculation tool.

FIG. 11 illustrates another example interface 1100 that may be used by a second operator to review submitted data. In particular embodiments, the interface 1100 of the MPR calculation tool can correspond to a "Block Compare" tab 1105 that facilitates the operator comparing values submitted for multiple blocks simultaneously. Interface 1100 includes two interactive components 1110*a* and 1110*b* that be used to review the submitted data for two blocks side-by-side. The data displayed can be similar to the data displayed in interfaces 800 and 900, including entered and calculated values. The second operator can select, using a drop-down or search element 1115*a* and 1115*b* which block the second operator would like to review. In particular embodiments, the second operator is not limited to just comparing separate blocks from the same subject but can also use a drop-down or search element 1120*a* and 1120*b* to change the subject for which the block information will be retrieved. As used herein, a block refers to a collection of samples from the same sample of tissue, or image of said tissue, corresponding to single point in time. Using the block comparison interface 1100, the second operator can compare multiple blocks across a range of samples, such as multiple blocks from the same subject, the same block across multiple points in time, blocks from multiple subjects, or event blocks across different clinical studies, where appropriate.

Figure 12:
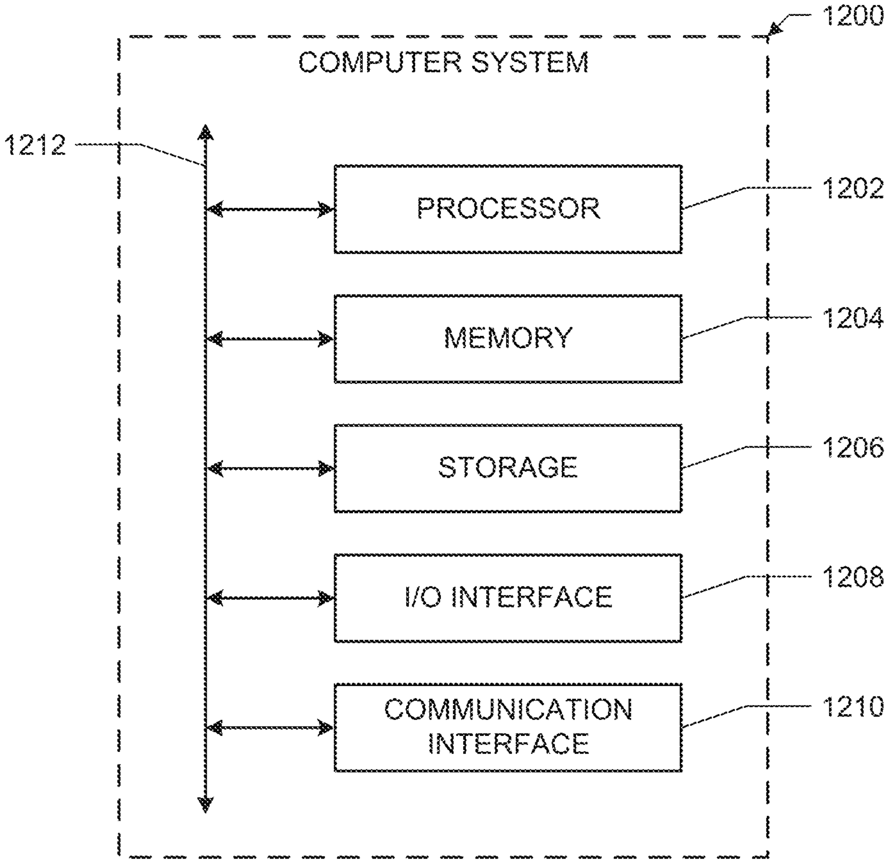
FIG. 12 illustrates an example computer system.

FIG. 12 illustrates an example computer system 1200. In particular embodiments, one or more computer systems 1200 perform one or more steps of one or more methods described or illustrated herein. In particular embodiments, one or more computer systems 1200 provide functionality described or illustrated herein. In particular embodiments, software running on one or more computer systems 1200 performs one or more steps of one or more methods described or illustrated herein or provides functionality described or illustrated herein. Particular embodiments include one or more portions of one or more computer systems 1200. Herein, reference to a computer system may encompass a computing device, and vice versa, where appropriate. Moreover, reference to a computer system may encompass one or more computer systems, where appropriate.

This disclosure contemplates any suitable number of computer systems 1200. This disclosure contemplates computer system 1200 taking any suitable physical form. As example and not by way of limitation, computer system 1200 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, a tablet computer system, an augmented/virtual reality device, or a combination of two or more of these. Where appropriate, computer system 1200 may include one or more computer systems 1200; be unitary or distributed; span multiple locations; span multiple machines; span multiple data centers; or reside in a cloud, which may include one or more cloud components in one or more networks. Where appropriate, one or more computer systems 1200 may perform without substantial spatial or temporal limitation one or more steps of one or more methods described or illustrated herein. As an example and not by way of limitation, one or more computer systems 1200 may perform in real time or in batch mode one or more steps of one or more methods described or illustrated herein. One or more computer systems 1200 may perform at different times or at different locations one or more steps of one or more methods described or illustrated herein, where appropriate.

In particular embodiments, computer system 1200 includes a processor 1202, memory 1204, storage 1206, an input/output (I/O) interface 1208, a communication interface 1210, and a bus 1212. Although this disclosure describes and illustrates a particular computer system having a particular number of particular components in a particular arrangement, this disclosure contemplates any suitable computer system having any suitable number of any suitable components in any suitable arrangement.

In particular embodiments, processor 1202 includes hardware for executing instructions, such as those making up a computer program. As an example and not by way of limitation, to execute instructions, processor 1202 may retrieve (or fetch) the instructions from an internal register, an internal cache, memory 1204, or storage 1206; decode and execute them; and then write one or more results to an internal register, an internal cache, memory 1204, or storage 1206. In particular embodiments, processor 1202 may include one or more internal caches for data, instructions, or addresses. This disclosure contemplates processor 1202 including any suitable number of any suitable internal caches, where appropriate. As an example and not by way of limitation, processor 1202 may include one or more instruction caches, one or more data caches, and one or more translation lookaside buffers (TLBs). Instructions in the instruction caches may be copies of instructions in memory 1204 or storage 1206, and the instruction caches may speed up retrieval of those instructions by processor 1202. Data in the data caches may be copies of data in memory 1204 or storage 1206 for instructions executing at processor 1202 to operate on; the results of previous instructions executed at processor 1202 for access by subsequent instructions executing at processor 1202 or for writing to memory 1204 or storage 1206; or other suitable data. The data caches may speed up read or write operations by processor 1202. The TLBs may speed up virtual-address translation for processor 1202. In particular embodiments, processor 1202 may include one or more internal registers for data, instructions, or addresses. This disclosure contemplates processor 1202 including any suitable number of any suitable internal registers, where appropriate. Where appropriate, processor 1202 may include one or more arithmetic logic units (ALUs); be a multi-core processor; or include one or more processors 1202. Although this disclosure describes and illustrates a particular processor, this disclosure contemplates any suitable processor.

In particular embodiments, memory 1204 includes main memory for storing instructions for processor 1202 to execute or data for processor 1202 to operate on. As an example and not by way of limitation, computer system 1200 may load instructions from storage 1206 or another source (such as, for example, another computer system 1200) to memory 1204. Processor 1202 may then load the instructions from memory 1204 to an internal register or internal cache. To execute the instructions, processor 1202 may retrieve the instructions from the internal register or internal cache and decode them. During or after execution of the instructions, processor 1202 may write one or more results (which may be intermediate or final results) to the internal register or internal cache. Processor 1202 may then write one or more of those results to memory 1204. In particular embodiments, processor 1202 executes only instructions in one or more internal registers or internal caches or in memory 1204 (as opposed to storage 1206 or elsewhere) and operates only on data in one or more internal registers or internal caches or in memory 1204 (as opposed to storage 1206 or elsewhere). One or more memory buses (which may each include an address bus and a data bus) may couple processor 1202 to memory 1204. Bus 1212 may include one or more memory buses, as described below. In particular embodiments, one or more memory management units (MMUs) reside between processor 1202 and memory 1204 and facilitate accesses to memory 1204 requested by processor 1202. In particular embodiments, memory 1204 includes random access memory (RAM). This RAM may be volatile memory, where appropriate. Where appropriate, this RAM may be dynamic RAM (DRAM) or static RAM (SRAM). Moreover, where appropriate, this RAM may be single-ported or multi-ported RAM. This disclosure contemplates any suitable RAM. Memory 1204 may include one or more memories 1204, where appropriate. Although this disclosure describes and illustrates particular memory, this disclosure contemplates any suitable memory.

In particular embodiments, storage 1206 includes mass storage for data or instructions. As an example and not by way of limitation, storage 1206 may include a hard disk drive (HDD), a floppy disk drive, flash memory, an optical disc, a magneto-optical disc, magnetic tape, or a Universal Serial Bus (USB) drive or a combination of two or more of these. Storage 1206 may include removable or non-removable (or fixed) media, where appropriate. Storage 1206 may be internal or external to computer system 1200, where appropriate. In particular embodiments, storage 1206 is non-volatile, solid-state memory. In particular embodiments, storage 1206 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. This disclosure contemplates mass storage 1206 taking any suitable physical form. Storage 1206 may include one or more storage control units facilitating communication between processor 1202 and storage 1206, where appropriate. Where appropriate, storage 1206 may include one or more storages 1206. Although this disclosure describes and illustrates particular storage, this disclosure contemplates any suitable storage.

In particular embodiments, I/O interface 1208 includes hardware, software, or both, providing one or more interfaces for communication between computer system 1200 and one or more I/O devices. Computer system 1200 may include one or more of these I/O devices, where appropriate. One or more of these I/O devices may enable communication between a person and computer system 1200. As an example and not by way of limitation, an I/O device may include a keyboard, keypad, microphone, monitor, mouse, printer, scanner, speaker, still camera, stylus, tablet, touch screen, trackball, video camera, another suitable I/O device or a combination of two or more of these. An I/O device may include one or more sensors. This disclosure contemplates any suitable I/O devices and any suitable I/O interfaces 1208 for them. Where appropriate, I/O interface 1208 may include one or more device or software drivers enabling processor

1202 to drive one or more of these I/O devices. I/O interface 1208 may include one or more I/O interfaces 1208, where appropriate. Although this disclosure describes and illustrates a particular I/O interface, this disclosure contemplates any suitable I/O interface.

In particular embodiments, communication interface 1210 includes hardware, software, or both providing one or more interfaces for communication (such as, for example, packet-based communication) between computer system 1200 and one or more other computer systems 1200 or one or more networks. As an example and not by way of limitation, communication interface 1210 may include a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface 1210 for it. As an example and not by way of limitation, computer system 1200 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, computer system 1200 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination of two or more of these. Computer system 1200 may include any suitable communication interface 1210 for any of these networks, where appropriate. Communication interface 1210 may include one or more communication interfaces 1210, where appropriate. Although this disclosure describes and illustrates a particular communication interface, this disclosure contemplates any suitable communication interface.

In particular embodiments, bus 1212 includes hardware, software, or both coupling components of computer system 1200 to each other. As an example and not by way of limitation, bus 1212 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination of two or more of these. Bus 1212 may include one or more buses 1212, where appropriate. Although this disclosure describes and illustrates a particular bus, this disclosure contemplates any suitable bus or interconnect.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes and illustrates respective embodiments herein as including particular components, elements, feature, functions, operations, or steps, any of these embodiments may include any combination or permutation of any of the components, elements, features, functions, operations, or steps described or illustrated anywhere herein that a person having ordinary skill in the art would comprehend. Furthermore, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative. Additionally, although this disclosure describes or illustrates particular embodiments as providing particular advantages, particular embodiments may provide none, some, or all of these advantages.

What is claimed is:

1. A method comprising:

receiving one or more images corresponding to a set of samples;

generating, based on the one or more images, one or more sets of parameters, each set of the one or more sets of the parameters comprising dimensions of a sample area of a respective sample, a percentage of the sample area of the respective sample comprising viable cells, a percentage of the sample area of the respective sample comprising necrosis, a percentage of the sample area of the respective sample comprising stroma, or any combination thereof;

displaying, via a first user interface of a computing device, the one or more sets of parameters;

receiving at least one user input indicative of a confirmation or a modification of the one or more sets of parameters;

determining, based on the at least one user input and the one or more sets of parameters, that a weighted percentage of viable cells in the set of samples satisfies a threshold condition, wherein the weighted percentage of viable cells is determined using a set of weights corresponding to the set of samples, each weight of the set of weights corresponding to a measurement associated with a respective sample of the set of samples;

in accordance with a determination that the weighted percentage of viable cells in the set of samples satisfies the threshold condition, determining that a specified condition is detected in the set of samples; and displaying, via a second user interface of the computing device, the specified condition.

2. The method of claim 1, wherein the generating the one or more sets of parameters comprises applying one or more computer vision models to the one or more images.

3. The method of claim 1, wherein the at least one user input is received in response to a prompt requesting review of the one or more images, the one or more sets of parameters, or both.

4. The method of claim 1, wherein the specified condition is determined further based on an average percentage of viable cells in the set of samples satisfying a second threshold condition.

5. The method of claim 1, further comprising in response to detecting one or more errors in the one or more sets of parameters, displaying a prompt requesting correction of the one or more errors, wherein the user input indicative of the modification is received in response to the prompt.

6. The method of claim 5, wherein the one or more errors comprise:

a percentage greater than 100%;

missing data values;

incomplete data values;

dimensions of the sample area failing to satisfy a threshold sample area;

a value of the one or more sets of parameters exceeding a specified range; or any combination thereof.

7. The method of claim 5, wherein displaying the prompt requesting correction of the one or more errors comprises displaying indications corresponding to the one or more errors.

8. The method of claim 7, wherein:

the one or more errors comprise a first type of error and a second type of error; and the displaying the indications corresponding to the one or more errors comprises displaying a first indication for the first type of error and displaying a second indication for the second type of error.

9. The method of claim 1, wherein the generating the one or more sets of parameters comprises receiving a portion of the one or more sets of parameters via one or more inputs to a third user interface of the computing device.

10. The method of claim 1, wherein the one or more images correspond to a sample of the set of samples.

11. The method of claim 10, further comprising displaying, via the first user interface, one or more identifiers of the sample.

12. The method of claim 1, further comprising in response to selection of a user interface object of the second user interface, transmitting, by the computing device, the specified condition to a second computing device.

13. The method of claim 1, further comprising in response to selection of a user interface object of the second user interface, transmitting, by the computing device, the one or more sets of parameters to a second computing device.

14. The method of claim 1, further comprising displaying, via the second user interface, the weighted percentage of viable cells in the set of samples, a non-weighted percentage of viable cells in the set of samples, an average percentage of sample areas of the set of samples comprising necrosis, an average percentage of sample areas of the set of samples comprising stroma, a total assessed area of the set of samples, or any combination thereof.

15. The method of claim 1, wherein:

the weighted percentage is determined based on each sample area of the respective sample relative to a total area of the set of samples; and the satisfying of the threshold condition indicates occurrence of the specified condition.

16. The method of claim 15, wherein:

a ratio between the each sample area of the respective sample to the total sample area of the set of samples is a weighting factor of the respective sample; and the weighted percentage is determined by:

applying each weighting factor to the percentage of the sample area of the respective sample comprising viable cells to generate an individual weighted percentage of the respective sample; and summing the individual weighted percentages.

17. The method of claim 1, further comprising displaying, via the first user interface, the one or more images.

18. The method of claim 1, further comprising in response to a selection of a user interface element of the first interface, displaying a third user interface of the computing device for receiving one or more sets of second parameters corresponding to a second set of samples.

19. A system comprising:

one or more processors; and one or more computer-readable non-transitory storage media coupled to one or more of the processors and comprising instructions operable when executed by one or more of the processors to cause the system to perform operations comprising:

receiving one or more images corresponding to a set of samples;

generating, based on the one or more images, one or more sets of parameters, each set of the one or more sets of the parameters comprising dimensions of a sample area of a respective sample, a percentage of the sample area of the respective sample comprising viable cells, a percentage of the sample area of the respective sample comprising necrosis, a percentage of the sample area of the respective sample comprising stroma, or any combination thereof;

displaying, via a first user interface of a computing device, the one or more sets of parameters;

receiving at least one user input indicative of a confirmation or a modification of the one or more sets of parameters;

determining, based on the at least one user input and the one or more sets of parameters, that a weighted percentage of viable cells in the set of samples satisfies a threshold condition, wherein the weighted percentage of viable cells is determined using a set of weights corresponding to the set of samples, each weight of the set of weights corresponding to a measurement associated with a respective sample of the set of samples;

in accordance with a determination that the weighted percentage of viable cells in the set of samples satisfies the threshold condition, determining that a specified condition is detected in the set of samples; and displaying, via a second user interface of the computing device, the specified condition.

20. A non-transitory computer-readable medium storing one or more instructions, which, when executed by one or more processors of one or more computing devices, cause the computing devices to perform a method comprising:

receiving one or more images corresponding to a set of samples;

generating, based on the one or more images, one or more sets of parameters, each set of the one or more sets of the parameters comprising dimensions of a sample area of a respective sample, a percentage of the sample area of the respective sample comprising viable cells, a percentage of the sample area of the respective sample comprising necrosis, a percentage of the sample area of the respective sample comprising stroma, or any combination thereof;

displaying, via a first user interface of a computing device, the one or more sets of parameters;

receiving at least one user input indicative of a confirmation or a modification of the one or more sets of parameters;

determining, based on the at least one user input and the one or more sets of parameters, that a weighted percentage of viable cells in the set of samples satisfies a threshold condition;

wherein the weighted percentage of viable cells is determined using a set of weights corresponding to the set of samples, each weight of the set of weights corresponding to a measurement associated with a respective sample of the set of samples;

in accordance with a determination that the weighted percentage of viable cells in the set of samples satisfies the threshold condition, determining that a specified condition is detected in the set of samples; and displaying, via a second user interface of the computing device, the specified condition.

* * * * *